United States Patent
Tagge et al.

(10) Patent No.: US 7,033,840 B1
(45) Date of Patent: Apr. 25, 2006

(54) REACTION CALORIMETER AND DIFFERENTIAL SCANNING CALORIMETER FOR THE HIGH-THROUGHPUT SYNTHESIS, SCREENING AND CHARACTERIZATION OF COMBINATORIAL LIBRARIES

(75) Inventors: Christopher D. Tagge, San Carlos, CA (US); Robert B. Wilson, Jr., Palo Alto, CA (US); Seajin Oh, Palo Alto, CA (US); Albert S. Hirschon, Menlo Park, CA (US)

(73) Assignee: SRI International, Menlo Park, CA (US)

( * ) Notice: Subject to any disclaimer, the term of this patent is extended or adjusted under 35 U.S.C. 154(b) by 566 days.

(21) Appl. No.: 09/708,687

(22) Filed: Nov. 9, 2000

Related U.S. Application Data
(60) Provisional application No. 60/167,227, filed on Nov. 24, 1999, and provisional application No. 60/164,342, filed on Nov. 9, 1999.

(51) Int. Cl.
    G01N 25/20 (2006.01)
    G01N 31/10 (2006.01)

(52) U.S. Cl. .................. 436/147; 422/51; 422/68.1; 422/99; 422/103; 422/104; 436/37; 436/183

(58) Field of Classification Search ............. 422/51, 422/68.1, 99, 103, 104; 436/37, 147, 183
    See application file for complete search history.

(56) References Cited

U.S. PATENT DOCUMENTS
3,211,531 A  10/1965  Benzinger et al.

(Continued)

FOREIGN PATENT DOCUMENTS
EP  0 810 030 A  12/1997
EP  0 882 500 A  12/1998

(Continued)

OTHER PUBLICATIONS
Verhaegen et al. SPIE 1999, 3606, 20–27.*

(Continued)

Primary Examiner—Arlen Soderquist
(74) Attorney, Agent, or Firm—Nixon Peabody, LLP

(57) ABSTRACT

Workstation, apparatuses and methods for the high-throughput synthesis, screening and/or characterization of combinatorial libraries. The invention relates to an array, which permits various high-throughput methods for synthesis, screening and/or characterization in the same array, without requiring sample transfer from the array. In a preferred embodiment, the synthesis, screening, and/or characterization steps are carried out in a highly parallel fashion, where more than one compound is synthesized, screened, and/or characterized at the same time. The invention may be practiced at the microscale. The array may comprise thermal channels, for regulating the temperature of the wells in the array. The wells of the array may comprise a membrane, which is used in various screening and characterization methods. The invention also relates to a covered array, comprising the array and an array cover, as well as an apparatus comprising the array, which comprises the array, an array cover and a stage. The array, array cover, and the stage may be modified as required for a variety of synthesis and/or analysis techniques. The array is easily interchangeable between different analytical instruments, and in an embodiment, the invention relates to an automated workstation, where the array is transferred between different synthesis, screening, and characterization stations. The invention also relates to a variety of methods for synthesis, screening, and characterization, which are adapted for combinatorial chemistry. Any of the embodiments of the invention may be used either alone or taken in various combinations.

16 Claims, 22 Drawing Sheets

(8 of 22 Drawing Sheet(s) Filed in Color)

U.S. PATENT DOCUMENTS

| | | | |
|---|---|---|---|
| 3,431,077 A | 3/1969 | Danforth | 23/253 |
| 3,607,073 A | 9/1971 | Stamm | 23/230 |
| 3,814,769 A | 6/1974 | Hoey et al. | 260/288 |
| 4,075,092 A | 2/1978 | White et al. | |
| 4,099,923 A | 7/1978 | Milberger | 23/254 |
| 4,151,252 A * | 4/1979 | Marchand et al. | 422/51 |
| 4,246,339 A | 1/1981 | Cole et al. | |
| 4,383,438 A * | 5/1983 | Eaton | 73/61.2 |
| 4,422,151 A | 12/1983 | Gilson | 364/496 |
| 4,510,684 A | 4/1985 | Hutchins et al. | 29/703 |
| 4,642,220 A | 2/1987 | Bjorkman | |
| 4,673,651 A | 6/1987 | Rothenberg et al. | |
| 4,677,742 A | 7/1987 | Johnson | 29/591 |
| 4,704,255 A | 11/1987 | Jolley | |
| 4,733,073 A | 3/1988 | Becker et al. | 250/288 |
| 4,777,021 A | 10/1988 | Wertz et al. | |
| 4,786,601 A | 11/1988 | Rothenberg | |
| 4,789,804 A | 12/1988 | Karube et al. | 310/311 |
| 4,837,374 A | 6/1989 | Brown et al. | 422/130 |
| 4,874,500 A | 10/1989 | Madou et al. | 204/412 |
| 4,902,481 A | 2/1990 | Clark et al. | |
| 4,910,999 A * | 3/1990 | Eaton | 73/61.2 |
| 4,992,415 A | 2/1991 | Ashok et al. | 505/1 |
| 5,039,604 A | 8/1991 | Papsidero | |
| 5,088,316 A | 2/1992 | McKelvey et al. | 73/38 |
| 5,108,704 A | 4/1992 | Bowers et al. | |
| 5,116,496 A | 5/1992 | Scott | |
| 5,164,159 A | 11/1992 | Hayashi et al. | 422/81 |
| 5,164,796 A | 11/1992 | Di Guiseppi et al. | |
| 5,224,775 A | 7/1993 | Reading et al. | 374/11 |
| 5,248,199 A | 9/1993 | Reading | 374/11 |
| 5,252,294 A | 10/1993 | Kroy et al. | 422/102 |
| 5,255,976 A | 10/1993 | Connelly | |
| 5,281,540 A | 1/1994 | Merkh et al. | 436/530 |
| 5,330,931 A | 7/1994 | Emesh et al. | 437/60 |
| 5,345,213 A | 9/1994 | Semancik et al. | 338/34 |
| 5,356,756 A * | 10/1994 | Cavicchi et al. | 430/315 |
| 5,403,680 A | 4/1995 | Otagawa et al. | 429/213 |
| 5,459,300 A | 10/1995 | Kasman | 219/433 |
| 5,463,564 A | 10/1995 | Agrafiotis et al. | 364/496 |
| 5,474,796 A | 12/1995 | Brennan | 427/2.13 |
| 3,245,758 A | 4/1996 | Benzinger et al. | |
| 5,508,200 A | 4/1996 | Tiffany et al. | 436/44 |
| 5,545,531 A | 8/1996 | Rava et al. | 435/6 |
| 5,609,826 A | 3/1997 | Cargill et al. | 422/99 |
| 5,668,303 A | 9/1997 | Giesler et al. | |
| 5,700,637 A | 12/1997 | Southern | 435/6 |
| 5,710,374 A | 1/1998 | Ross et al. | 73/54.24 |
| 5,712,171 A | 1/1998 | Zambias et al. | 436/518 |
| 5,714,127 A | 2/1998 | DeWitt et al. | 422/131 |
| 5,753,187 A | 5/1998 | Reynolds et al. | 422/102 |
| 5,759,493 A | 6/1998 | Raisanen | |
| 5,762,881 A | 6/1998 | Harness et al. | 422/132 |
| 5,770,157 A | 6/1998 | Cargill et al. | 422/99 |
| 5,783,805 A | 7/1998 | Katzmann | |
| 5,792,431 A | 8/1998 | Moore et al. | 422/134 |
| 5,800,231 A | 9/1998 | De Haas et al. | 445/24 |
| 5,821,596 A | 10/1998 | Miu et al. | |
| 5,834,195 A | 11/1998 | Benkovic et al. | 435/6 |
| 5,858,309 A | 1/1999 | Mathus et al. | 422/102 |
| 5,872,051 A | 2/1999 | Fallon et al. | 438/616 |
| 5,874,004 A | 2/1999 | DeWitt | |
| 5,880,972 A | 3/1999 | Horlbeck | 364/496 |
| 5,889,315 A | 3/1999 | Okumura et al. | 310/321 |
| 5,928,952 A | 7/1999 | Hutchins et al. | 436/50 |
| 5,955,373 A | 9/1999 | Hutchins et al. | 436/48 |
| 5,959,297 A | 9/1999 | Weinberg et al. | 250/288 |
| 5,961,925 A | 10/1999 | Ruediger et al. | 422/99 |
| 5,976,470 A | 11/1999 | Maiefski et al. | 422/103 |
| 5,985,214 A | 11/1999 | Stylli et al. | 422/65 |
| 5,985,356 A | 11/1999 | Schultz et al. | 427/8 |
| 5,985,551 A | 11/1999 | Brennan | 435/6 |
| 6,004,617 A | 12/1999 | Schultz et al. | 427/8 |
| 6,030,917 A | 2/2000 | Weinberg et al. | 502/104 |
| 6,034,775 A | 3/2000 | McFarland et al. | 356/364 |
| 6,044,212 A | 3/2000 | Flavin et al. | 395/500.27 |
| 6,045,671 A | 4/2000 | Wu et al. | 204/298.11 |
| 6,045,755 A | 4/2000 | Lebl et al. | 422/65 |
| 6,054,100 A | 4/2000 | Stanchfield et al. | |
| 6,063,633 A * | 5/2000 | Willson, III | 436/37 |
| 6,086,831 A | 7/2000 | Harness et al. | 422/199 |
| 6,087,181 A | 7/2000 | Cong | 436/37 |
| 6,183,645 B1 | 2/2001 | DeWitt | |
| 6,306,658 B1 * | 10/2001 | Turner et al. | 436/37 |
| 6,309,605 B1 | 10/2001 | Zermani | |
| 6,428,749 B1 | 8/2002 | Kajiyama et al. | |
| 6,438,497 B1 | 8/2002 | Mansky et al. | |
| 6,485,913 B1 | 11/2002 | Becker et al. | |
| 6,535,824 B1 | 3/2003 | Mansky et al. | |

FOREIGN PATENT DOCUMENTS

| | | |
|---|---|---|
| EP | 0 905 515 A | 3/1999 |
| EP | 0 921 391 A1 | 6/1999 |
| EP | 0 978 499 A | 2/2000 |
| WO | WO 95/28640 | 10/1995 |
| WO | WO 98/52047 | 11/1996 |
| WO | WO 97/28168 | 8/1997 |
| WO | WO 97/32208 | 9/1997 |
| WO | WO 97/37953 | 10/1997 |
| WO | WO 97/40181 | 10/1997 |
| WO | WO 97/42500 | 11/1997 |
| WO | WO 97/43611 | 11/1997 |
| WO | WO 98/03521 | 1/1998 |
| WO | WO 98/08077 | 2/1998 |
| WO | WO 98/14277 | 4/1998 |
| WO | WO 98/15501 | 4/1998 |
| WO | WO 98/15805 | 4/1998 |
| WO | WO 98/15813 | 4/1998 |
| WO | WO 98/15969 | 4/1998 |
| WO | WO 98/16830 | 4/1998 |
| WO | WO 98/17382 | 4/1998 |
| WO | WO 98/39099 | 9/1998 |
| WO | WO 98/40159 | 9/1998 |
| WO | WO 99/03684 | 1/1999 |
| WO | WO 99/05318 | 2/1999 |
| WO | WO 99/15905 | 4/1999 |
| WO | WO 99/18431 | 4/1999 |
| WO | WO 99/19724 | 4/1999 |
| WO | WO 99/24834 | 5/1999 |
| WO | WO 99/41005 | 8/1999 |
| WO | WO 99/51546 | 10/1999 |
| WO | WO 99/51980 | 10/1999 |
| WO | WO 99/64160 | 12/1999 |
| WO | WO 00/09255 | 2/2000 |
| WO | WO 00/17413 | 3/2000 |
| WO | WO 00/20377 | 4/2000 |
| WO | WO 00/36410 | 6/2000 |
| WO | WO 00/40331 | 7/2000 |
| WO | WO 00/79254 | 12/2000 |

OTHER PUBLICATIONS

McNeil & Straiton, "Copolymerization of Methyl Methacrylate with $^{36}$Cl–Vinyl Chloride," *European Polymer Journal*, vol. 13 (1997) pp. 17–18.

Schröder & Schöön, "Radioactive Tracer Techniques for Study of Reactions on Industrial Catalysts," *Journal of Catalysis*, vol. 143 (1993) pp. 381–387.

Anderson, et al., "Imaging of hydrocarbon reactions in zeolite packed–bed reactors using positron emission profiling," *Catalysis Letters*, vol. 56, No. 2/03, Dec. 1998, pp. 137–144.

Hauden, et al., "Capteurs résonnants à ondes élastiques de surface," *Onde Electrique*, vol. 74, No. 2, Mar. 1, 1994, pp. 43–47.

Martin, et al., "Viscosity and Density Sensing with Ultrasonic Plate Waves," *Sensors and Actuators*, vol. A22, No. 1/03, Mar. 1, 1990, pp. 704–708.

Mayer, et al., "Nanotiterplates for Screening and Synthesis", *BioMethods*, 10:75–128 (1999).

D. E. Akporiaye, et al., "Combinatorial Approach to the Hydrothermal Synthesis of Zeolites", *Angew. Chem. Intl. Ed.*, 37:609–11 (1998).

Ayre, L. Moro, C. H. Becker, "Effects of Desorption Method and Photoionizing Laser Characteristics on Molecular Fragmentation", Anal. Chem. (1994), 66(10): 1610–19 (1994).

Becker, L. E. Jusinski, L. Moro, "Infrared Laser–Induced Desorption of Neutral Organic Compounds from Frozen Aqueous Solution Followed By Single–Photon Ionization", Int. J. Mass Spec. Ion Proc. 95:R1–R4 (1990).

Becker, Fresenius, "On the use of single–photon ionization for inorganic surface analysis", J. Anal. Chem., 341:3–6 (1991).

Bekman, I. N., et al., "Radioactive Gases for Decorating Structures in Polymers", *Radiokhimiya* 28(2):198–203 (1986).

Bellazzini, R. et al., "High Resolution Digital Autoradiography or Short and Long Range B–Emitters Using a Single Step Parallel Plate Chamber", *Nucl. Instrum. Methods Phys. Res. Sect.* A251:196–8 (1986).

Berkoff, et al., "A Multiple Cell Apparatus for the Rapid Evaluation of Catalysed Chemical Reactions", *Chemistry and Industry*, 68–69 (Jan. 17, 1981).

Boone, "Thermal Microsensors for Environmental and Industrial Controls", NIST Workshop on "Gas Sensors Strategies for Future Technology" Gaithersburg, MD Sep. 8–9, (1993).

Burbaum and Sigal, "New Technologies for High–Throughput Screening", *Combinatorial Chemistry*, 72–78 (1997).

Chen, B. Guo, "Use of Binary Solvent Systems in the MALDI–TOF Analysis of Poly(methyl methacrylate)", Anal. Chem., 69(21): 4399–4404.

Corkan, et al., "Application of an Automated Chemistry Workstation to Problems in Synthetic Chemistry", *Chemometrics and Intelligent Laboratory Systems, Laboratory Information Management*, 17:95–105 (1992).

Corkan and Lindsey, "Experiment Manager Software for an Automated Chemistry Workstation, Including a Schedule for Parallel Experimentation", *Chemometrics and Intelligent Laboratory Systems, Laboratory Information Management*, 17:47–74 (1992).

M. S. deVries et al., "Vacuum UV photoionization mass spectrometyr of small polymers using jet cooling", J. Photochemistry and Photobiology A: Chemistry 106:31–36 (1997).

Figge, K. et al., "Migration von Hilfsstoffen der Kunststoffverarbeitung as Folien in flussige und feste Fette bzw. Simulantien", *Duete Lebensmittel–Rundschau*, 66(9):281–9 (1970) (only summary in English).

Frazer, "Automated Chemical Instrumentation of the Future", *Automated Chemical Instrumentation*, 7(5):141–147 (1974).

Frisbee, et al., "Robotic Orchestration of Organic Reactions: Yield Optimization Via an Automated System with Operator–Specified Reaction Sequences", *J. Am. Chem. Soc.*, 106:7143–7145 (1984).

Grisel and Demarne, "Fabrication of Integrated Thin Film Semiconductor Gas Sensors", *Chemical Sensor Technology*, vol. 2 (1989).

Guette, et al., "Automation in the Organic Chemistry Laboratory: Why? How?", *Pure & Appl. Chem.*, 60(11);1669–1678 (1988).

Hanak, "The 'Multiple–Sample Concept' in Materials Research: Synthesis, Compositional Analysis and Testing of Entire Multicomponent Systems", *Journal of Materials Science*, 5:964–971 (1970).

Jackson et al., "Matrix–Assisted Laser Description/Ionization–Collision Induced Dissoaciation of Poly(Styrene)", J. Am. Soc. Mass Spectrom., 9(4):269–74 (1998).

Karas, D. Bachmann, F. Hillenkamp, "Influence of the Wavelength in High–Irradiance Ultraviolet Laser Desorption Mass Spectrometry of Organic Molecules", Anal. Chem., 57:2935–39 (1985).

Katz, "Oxidation", *VSLI Technology*, 131–167.

Klein, et al., "Combinatorial Material Libraries on the Microgram Scale with an Example of Hydrothermal Synthesis", *Angew. Chem. Intl. Ed.*, 37(24):3369–72 (1998).

Ko, et al., "Bonding Techniques and Microsensors", *Micromachining and Micropackaging of Transducers*, 198–208 (1985).

Krebs and Grisel, "A Low Power Integrated Catalytic Gas Sensor", *Microsens S.A.*, Switzerland (1992).

Lam, "Application of Combinatorial Library Methods in Cancer Research and Drug Discovery", *Anti Cancer Drug Design*, 12:145–167 (1997).

Lindsey, "A Restrospective on the Automation of Laboratory Synthetic Chemistry", *Chemometrics and Intelligent Laboratory Systems, Laboratory Information Management*, 17:15–45 (1992).

McGillis, "Lithography", *VSLI Technology*, 267–301.

Moates, et al., "Infrared Thermographic Screening of Combinatorial Libraries of Heterogeneous Catalysts", *Ind. Eng. Chem. Res.*, 35:4801–4803 (1996).

Morris, et al., "Automation of Protein Crystallization Trials: Use of a Robot in Deliver Reagents to a Novel Multi–Chamber Vapor Diffusion Plate", *Product Application Focus*, 7(5):522–527 (1989).

Mouncey, L. Moro, C. H. Becker, "High spatial chemical imaging of surfaces by combinaiton of a field–emission ion gun and intense laser radiation", *Appl. Surf. Science* 52:39–44 (1991).

Mysak, F. et al., "Anyagokban lévó repedések autoradiográfias vizigálato", *Izotoptechnika*, 14(1–2):27–28 (1971) (only abstract in English).

Pallix, U. Schuhle, C. H. Becker, D. L. Huestis, "Advantages of Single–Photon Ionization over multiphoton Ionization for Mass Spectrometric Surface Analysis of Bulk Organic Polymers", Anal. Chem. 61:805–11 (1989).

Pearce, "Epitaxy", *VSLI Technology*, 5–92.

R. E. Pelrine et al., "Electrostriction of Polymer Films for Microactuators", Proceedings of the 10th Annual IEEE International Workshop on Microelectrode Mechanical Systems, Nagoya, Japan, pp. 238–243 (1997).

Petersen, "Silicon as a Mechanical Material", *Proc. IEEE*, 70(5):420–457 (1982).

Plouvier, et al., "Experiment Planner for Strategic Experimentation with an Automated Chemistry Workstation", *Chemometrics and Intelligent Laboratory Systems: Laboratory Information Management*, 17:75–94 (1992).

S. M. Senkan, et al., "Discovery and Optimization of Heterogeneous Catalysts by Using Combinatorial Chemistry", *Angew. Chem. Intl. Ed.*, 38(6):791–95.

Senturia, "Microfabricated Structures for the Measurement of Mechanical Properties and Adhesion of Thin Films", *Transducers '87, Rec. of the 4$^{th}$ Int. Conf. On Solid–State Sensors and Actuators*, 11–16 (1987).

Snyder, et al., "Automated Update on Chemical Continous Flow Approach Analysis", *Analytical Chemistry*, 48(12):942A–956A (1976).

Taylor and Marks, "Pharmaceutical Industry Screening for New Antiepileptic Drugs", *Antiepileptic Drug Development, Advances in Neurology*, 76:41–47 (1998).

Visser, et al., "Catalytic Calorimetric Gas Sensors", 5$^{th}$ International Meeting on Chemical Sensors, Jul. 11–14, 1994 Rome, Italy (1994).

Zanini, et al., "Fabrication and Properties of a Si–basded High Sensitivity Microcalorimetric Gas Sensor", *Solid–State Sensors and Actuator Workshop*, Ford Research Laboratory, MD (1994).

Zuckermann, et al., "Design, Construction and Application of a Fully Automated Equimolar Peptide Mixture Synthesizer", *Int. J. Peptide Protein Res.*, 40:497–506 (1992).

\* cited by examiner

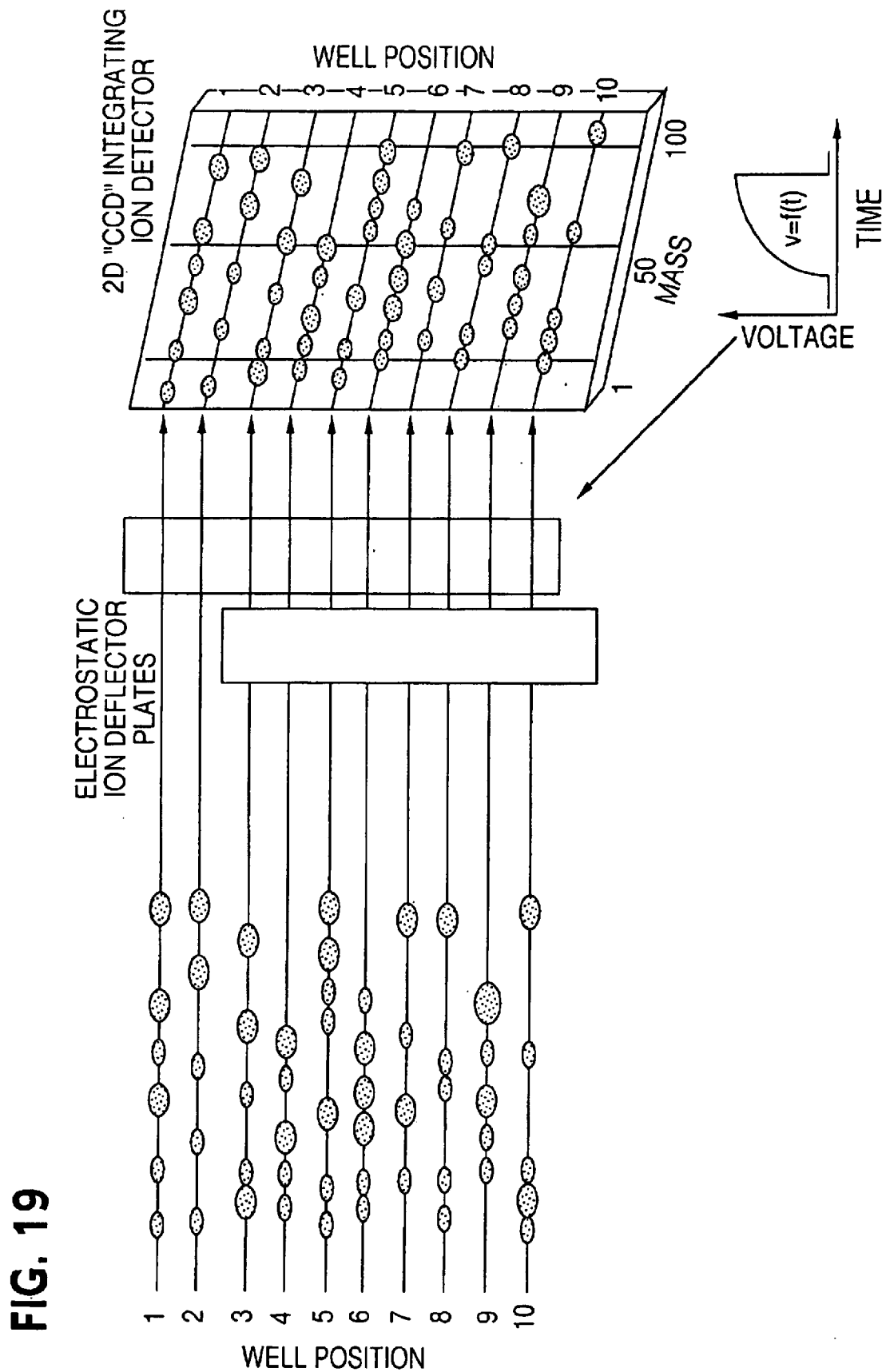

REACTION CALORIMETER AND DIFFERENTIAL SCANNING CALORIMETER FOR THE HIGH-THROUGHPUT SYNTHESIS, SCREENING AND CHARACTERIZATION OF COMBINATORIAL LIBRARIES

This application claims benefit under 35 U.S.C. §119 to U.S. Provisional Application Nos. 60/164,342 filed Nov. 9, 1999 and 60/167,227 filed Nov. 24, 1999; the disclosure of both these applications is hereby incorporated by reference in their entirety.

FIELD OF INVENTION

This invention relates to a workstation, apparatus and methods for the high-throughput synthesis, screening and/or characterization of combinatorial libraries. The invention includes a workstation, an array, a covered array, and an apparatus comprising the array, as well as methods for using and making these. These methods include the use of an array, which may be transferred between a series of different synthesis, screening, or characterization stations.

BACKGROUND OF THE INVENTION

The use of combinatorial techniques to generate libraries of chemical and/or biological compounds is known in the art. Once these libraries have been generated, it is necessary to screen or characterize the compounds to determine if the desired properties are present, i.e. physical, chemical and/or biological properties, for example. However, most techniques developed for screening and characterization of combinatorial libraries are sequential, involve sample preparation or sample transfer steps, and are generally labor-intensive, time-consuming and expensive for large libraries or arrays of several compounds.

What is needed in the art are apparatus and methods for high-throughput multiple parallel synthesis, followed by high-throughput screening and characterization of individual components in arrays or combinatorial libraries. In addition, these techniques should preferably be easily adapted to microscale techniques. Further, these techniques and apparatuses should be adaptable not only to areas where combinatorial chemistry is commonly used, such as pharmaceutical, biotechnology, and agrochemical research, but also to a broad range of disciplines, including catalysis and polymer chemistry.

Methods and apparatus for screening diverse arrays of materials in parallel using infrared imaging techniques are described in WO 98/15813. WO 97/32208 describes a catalyst testing process and apparatus, which includes methods and apparatus for parallel testing of catalysts. Despite these developments, there remains a need for techniques for the synthesis, screening, and characterization of individual compounds of a combinatorial library in the same array in a highly parallel fashion, without requiring the transfer of compounds from the array for analysis. This invention answers this need.

Moreover, the analysis of physical properties such as viscosity have yet to be adapted to combinatorial arrays, in a highly parallel manner and as applied to a broad range of compounds. WO 98/15501 describes systems and methods for characterization of materials and combinatorial libraries with mechanical oscillators. However, it does not appear that these methods would be generally adaptable to compounds other than liquids. U.S. Pat. No. 5,710,374 describes an electronic viscometer, and U.S. Pat. No. 5,889,351 describes a device for measuring viscosity and a device for measuring characteristics of fluid, but neither of these is designed or adapted for analysis of compounds other than liquids, or for combinatorial analysis of arrays. Work on electrostrictive principles has been reported in R. E. Pelrine et al., Proceedings of the $10^{th}$ Annual IEEE International Workshop on Microelectrode Mechanical Systems, Nagoya, Japan, pp. 238–243. However, this work has not been adapted for combinatorial chemistry. Also recently reported in WO 98/15501 is a combinatorial method to measure the molecular weight and molecular weight distribution of polystyrene in situ, using an array of vibrating reeds. However, this vibrating reed technique measures only the viscosity of the polymer mixture in solution. Accordingly, what is needed in the art are combinatorial techniques for measuring the viscosity of samples in arrays, and techniques for measuring viscosity which are not restricted to liquids. This invention answers this need.

Also needed in the art are combinatorial techniques for measuring the comonomer content of compounds. Although WO 97/37953 describes mass-based encoding and qualitative analysis of combinatorial libraries, these techniques are used primarily as a means for encoding, and are not adapted to quantitative analysis of the comonomer content of compounds or incorporation of a reagent, for compounds synthesized in combinatorial libraries. Polymer composition has not been investigated using radiography. Cracks and formations in polymer films have been investigated by diffusing a radiolabeled gas or liquid into a preformed polymer and scanning the sample using radiography. (See e.g., Figge, K. et al., *Deut. lebensm-Rundsch* 66(9):281–9 (1970), Bellazzini, R. et al., *Nucl. Instrum. Methods Phys. Res. Sect. A A*251(1):196–8 (1986), Mysak, F. et al., *Izotoptechnika*, 14(1–2):27–28 (1971), Bekman, I. N., et al. *Radiokhimiya* 28(2):222–229 (1986), and Kocbynka, D. et al., *Radioisotopy* 8(6):860–1 (1967)). Radiography has been used extensively for the rapid screening of biological samples. Yet, radiography has not been generally extended for the analysis of a variety of compounds. For example, polymer compositions (e.g., comonomer content) have never been investigated using radiography. Therefore, what is needed in the art is a technique for screening and characterization of combinatorial libraries that provides a qualitative and/or quantitative determination of comonomer content or incorporation of a reagent. This invention answers this need.

There have also been some developments in the characterization and screening of combinatorial libraries. For example, in-situ resonance enhanced multiphoton ionization (REMPI) spectroscopy has been demonstrated for rapid characterization of gaseous products produced by arrays of dehydrogenation catalysts. (S. M. Senkan, et al., *Angew. Chem. Intl. Ed*, 38:791 (1999)). In addition, techniques for the parallel screening of heterogeneous oxidation catalysts have been described in WO 98/15813 and WO 97/32208. Techniques for simultaneously measuring-catalyst activity and the molecular weight of the forming polymer in an array of 48 reactors has also been reported. (See U.S. Pat. No. 5,762,881 (1998)). Although these techniques have increased throughput in many cases, the relatively large reactor volume of the arrays and the capital investment to purchase new reactor blocks restricts the use of these arrays.

Although methods and apparatus for surface diagnostics have been reported in U.S. Pat. No. 4,733,073, these methods have not yet been adapted to the analysis of combinatorial libraries. U.S. Pat. No. 5,959,297 teaches mass spectrometers and methods for rapid screening of different materials. However, these methods appear to be slow and are not run under realistic process conditions. Therefore, what is needed in the art are mass spectrometry techniques which are run under realistic process conditions. Similarly, although method and apparatus for modulated differential analysis has been described in U.S. Pat. No. 5,224,775 and methods and apparatus for spatially resolved modulated differential analysis have been described in U.S. Pat. No. 5,248,199 these methods have not yet been adapted to the microscale or to combinatorial techniques. Methods for mass spectrometry, adapted to combinatorial chemistry are needed. This invention answers this need.

Adapting these combinatorial chemistry techniques to the microscale is particularly a challenge in fields such as catalysis and polymer chemistry. Catalytic olefin polymerization, for example, is sensitive to small variations in conditions and has rarely been attempted using microscale combinatorial techniques. However, if microscale combinatorial techniques could be adapted for use in these fields, this would significantly facilitate research and development, with the advantages of lower reagent costs, higher throughput, and greater efficiency.

There have been some attempts to adapt combinatorial synthesis techniques to the field of catalysis and polymer chemistry. In one case, combinatorial hydrothermal syntheses for zeolites was reported. (See D. E. Akporiaye, et al., *Angew. Chem. Intl. Ed.*, 37:609 (1998) and J. Klein, et al., *Angew. Chem. Intl. Ed.*, 37:3369 (1998)). However, high-throughput methods for screening and characterizing the components of the library, in the same apparatus used for the synthesis have not been described.

The combinatorial synthesis and analysis of supported and unsupported organometallic compounds and catalysts (e.g. homogeneous catalysts) has been described in WO 98/03521. In one embodiment, the substrate has an array of materials fixed thereon and the detector has X-Y motion. In another embodiment, the detector is fixed and the substrate having an array of materials thereon has R-θ motion. WO 98/15969 describes mass spectrometry and methods for rapid screening of libraries of different materials. However, for large combinatorial libraries, these sequential methods can be time-consuming and expensive. In addition, these methods are not adapted such that the compounds could be synthesized in the same array used for analysis.

What is needed are techniques which could efficiently screen and characterize libraries of polymers in a high-throughput manner. Further, these methods for screening and characterizing the polymer should preferably be adaptable to the microscale. This invention answers this need.

Accordingly, what is needed is a workstation, apparatus, and methods adapted for any combination of combinatorial synthesis, screening and/or characterization steps, without requiring excessive sample handling or transfer of components from the array between these steps. Preferably these methods will be non-consumptive, highly parallel, generally adaptable to the microscale, and generally applicable in many fields. Preferably, these techniques could be automated, such that the same array is moved between several different stations or analytical instruments. This invention answers this need.

SUMMARY

This invention relates to a workstation, apparatus, and methods for high-throughput synthesis, screening and characterization of individual compounds in combinatorial libraries. The invention also relates to an array having a plurality of wells, an apparatus comprising the array, or an automated workstation where the same array is moved between several different analytical instruments or stations, as well as methods for using these.

In one embodiment, the invention relates to an array which may be directly transferred between synthesis, screening, and characterization stations or instruments, preferably without requiring sample handling, sample preparation, or sample transfer steps. Preferably, the synthesis, screening, and characterization steps are carried out in a highly parallel manner, such that more than one compound is synthesized, screened and/or characterized at a time. Moreover, the array is also easily adapted to the microscale for several different types of reactions, including catalytic and polymerization reactions.

In an embodiment of the invention, the array has thermal channels, which may be metalized or doped, and are used to provide control of the thermal conditions within a well. The thermal channels may be present in a variety of arrangements. For example, at least one thermal channel may be aligned parallel to at least one of the rows or columns. In some embodiments, there may be two thermal channels on either side of the row of wells. It is also possible to provide different temperature ranges to different thermal channels. In another arrangement for the thermal channels, the wells are arranged in an array of rows and columns and the thermal channels define a checkerboard pattern around the wells; this arrangement is often used to provide isothermal conditions for synthesis or analysis.

In another embodiment of the invention, the bottom of the wells comprises a membrane layer, which is flexible, thermally conductive, or gas-permeable. The membrane will typically comprise at least one material selected from the group consisting of: silicon, doped silicon, silicon dioxide, doped silicon dioxide, steel, sapphire, a glass material, a ceramic material, or a plastic material. In a preferred embodiment, the membrane will comprise at least one material selected from silicon, doped silicon, steel, silicon nitride and silicon oxynitride. In a particularly preferred embodiment, the membrane will comprise at least one material selected from silicon and doped silicon. When doped silicon is used, the dopant is preferably boron, phosphorus, or arsenic. The membrane layer will typically be of a substantially uniform thickness. For instance, the membrane may have a thickness from about 100 nm to about 1 μm, from about 1 μm to about 50 μm, or from about 1 μm to about 20 μm.

In a another embodiment of the invention, the array comprises thermal channels and the wells in the array further comprise a membrane forming a layer at the bottom of the well. In this embodiment, the features of the thermal channels and the membrane layer are as described in other embodiments, and any additional features of any other embodiment, either taken alone, or in combination may be incorporated.

Further, this invention applies generally to both arrays of compounds or mixtures of compounds in combinatorial libraries. There may be individual compounds in each well, or mixtures of compounds. Moreover, the invention is not limited to fields such as pharmaceutical research, biotechnology, and agrochemistry, but may also be applied to a number of fields, including but not limited to, fields involving polymers, catalysts, superconductors, zeolites, magnetic materials, phosphors, thermoelectric materials, and high and low dielectric materials.

This invention relates to apparatus and methods for the high-throughput synthesis, screening and/or characterization of combinatorial libraries. In some embodiments, the invention relates to an array, a covered array, and/or an apparatus comprising the array. These apparatus are designed such that the array can be transferred between synthesis, screening and/or characterization operations, without requiring sample transfer from the array, or excessive sample preparation steps. In a preferred embodiment, the synthesis, screening, and/or characterization is carried out in a highly parallel fashion, where more than one compound or component of the library is synthesized, screened, and/or characterized at the same time. In a preferred embodiment, the invention is adapted to the micro scale.

The invention also relates to a covered array, comprising the array and an array cover, as well as an apparatus comprising the array, which comprises the array, an array cover and a stage. The array, array cover, and the stage may be interchanged or modified as needed for a particular application.

The invention also relates to a variety of methods for a combinatorial chemistry process, screening, and characterizing. In the combinatorial chemistry process, combinatorial libraries are synthesized in the array. After synthesis, the array may then be transferred to a number of screening and/or characterization stations. However, the invention is not limited to compounds synthesized in the array. For example, methods of the invention are not limited only to compounds synthesized in the array. Alternatively, compounds that have been previously synthesized or purchased, may be placed in the array for high-throughput screening and/or characterization.

The invention relates to a number of methods for the screening and/or characterization of compounds in a combinatorial library in the array. In one embodiment, the invention relates to a process for thermal imaging, where the heat generated in each well of the array is monitored in real time with a camera. This method may be used to screen and identify promising wells for further study and/or characterization. In another embodiment, the invention relates to a process for the parallel differential scanning calorimetry, where reactions may be run under isothermal conditions to obtain reaction kinetics data and thermodynamic data, for example. The invention also relates to methods for measuring the viscosity, stiffness and heat deflection temperature of compounds of the array by using an electrostatic interaction to induce vibrations of the silicon membrane, which are correlated to various physical properties of the compounds in each well. The invention also relates to methods for determining the incorporation of a labeled reagent into a product of the array by digital autoradiography; this method is particularly useful for techniques such as determining the co-monomer content of a polymer.

The invention relates to a workstation, comprising at least one stage to support at least one array, and at least one unit or analytical instrument. The array comprises a substrate having a plurality of wells. The unit or analytical instrument may be selected from any synthetic or analytical instrument, and is used for synthesis, screening and/or characterization of combinatorial libraries.

The workstation may further comprise means for transferring the array from a first analytical instrument to one or more other analytical instruments. The workstation may also comprise means for transferring the array, such as a robotic hand. In an embodiment of the invention, the workstation is automated. For instance, the array is bar-coded, and/or the workstation further comprises array hotels.

Any of the embodiments of the invention may be used either alone or taken in various combinations. Additional objects and advantages of the invention are discussed in the detailed description that follows, and will be obvious from that description, or may be learned by practice of the invention. It is to be understood that both this summary and the following detailed description are exemplary and explanatory only and are not intended to restrict the invention.

FIGURES

The patent or application file contains at least one drawing executed in color copies of this patent or patent application with color drawing(s) will be provided by the office upon request and payment of the necessary fee.

FIG. 1 illustrates the steps in a process for fabricating the array from a silicon wafer. This figure shows the following elements: (1) silicon wafer, (2) epitaxial layer, (3) silicon dioxide layer, (4) $Si_3N_4$ layer, (5) resist pattern, (6) thin metal film, (7) etching protective housing, (8) thermal channel, and (9) well. This process is described in greater detail in the specification.

FIG. 2 shows a cross-section of one embodiment of the array, and a magnification of a cross section of the membrane layer. In some embodiments, the membrane layer (10) is porous, as shown.

FIG. 3 shows a cross-section of an embodiment of the array, with the well (9) and thermal channels (8) shown. The gasket (11) is also shown, as well as the location of the membrane layer (10). In some embodiments, the thin metal film (12) will also be present.

FIG. 4 shows an embodiment of the array, where the substrate is stainless steel. The wells (9) are shown, as well as holes (13) for attaching the array in an apparatus, e.g. to an array cover, by a fastener such as a screw or a bolt. The well size in this figure is approximately 75 μL.

FIG. 5A and FIG. 5B show an embodiment of the array. A magnified view of the well (9) is shown in FIG. 5A. FIG. 5B shows a greater magnification of FIG. 5A, where the porosity of the membrane layer of the well is shown.

FIG. 6 is a magnification of the array shown in FIG. 5. FIG. 6A is a magnification of the view in FIG. 5B, where the porosity of the membrane layer is shown. FIG. 6B is a further magnification of FIG. 6A, where the porosity of the membrane layer is shown in greater detail.

Figure 10:
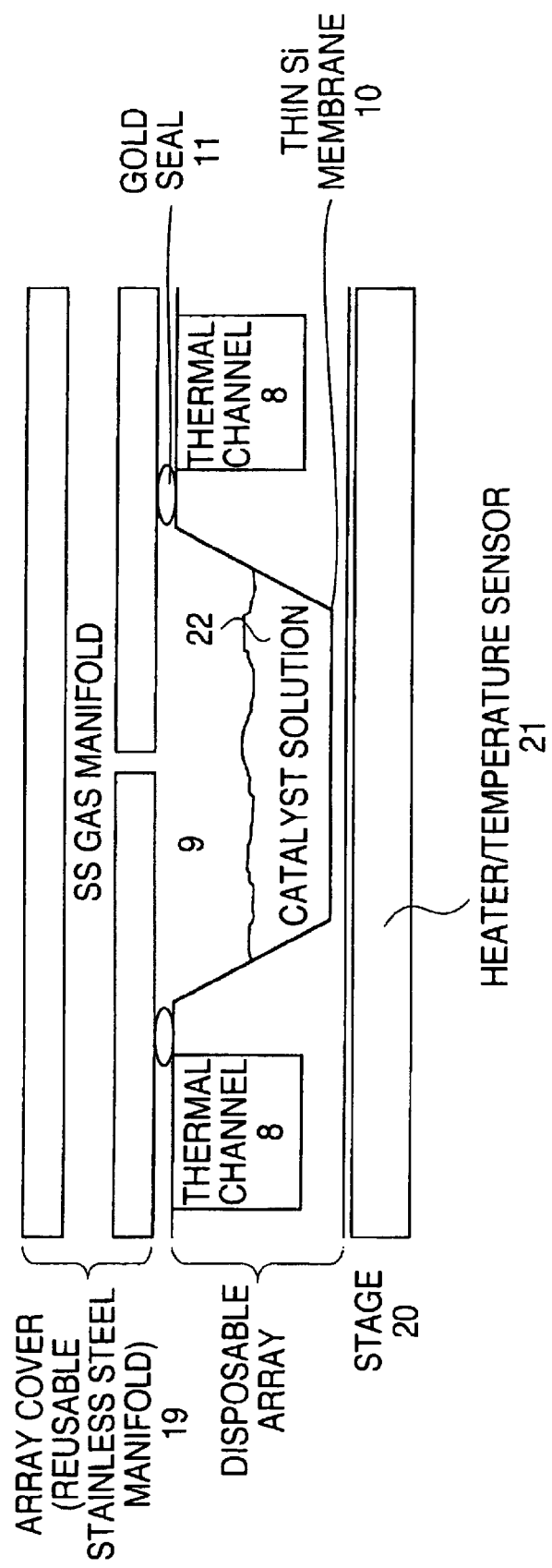

FIG. 10 shows a cross section of an embodiment of the array used for reaction calorimetry. As shown, the array comprises at least one reaction well (9), which contains a reaction mixture (22). There are thermal channels (8) surrounding the well (9), which are shown as cooling channels in this embodiment, and a gasket/gold seal (11) surrounding the edge of the well. In this embodiment, the wells comprise a thin silicon membrane forming the bottom of the well. The stage (20) further comprises a heater/temperature sensor (21). The array cover (19) comprises a reusable stainless steel gas manifold and, optionally, valves to inject solutions (not shown).

Figure 11:
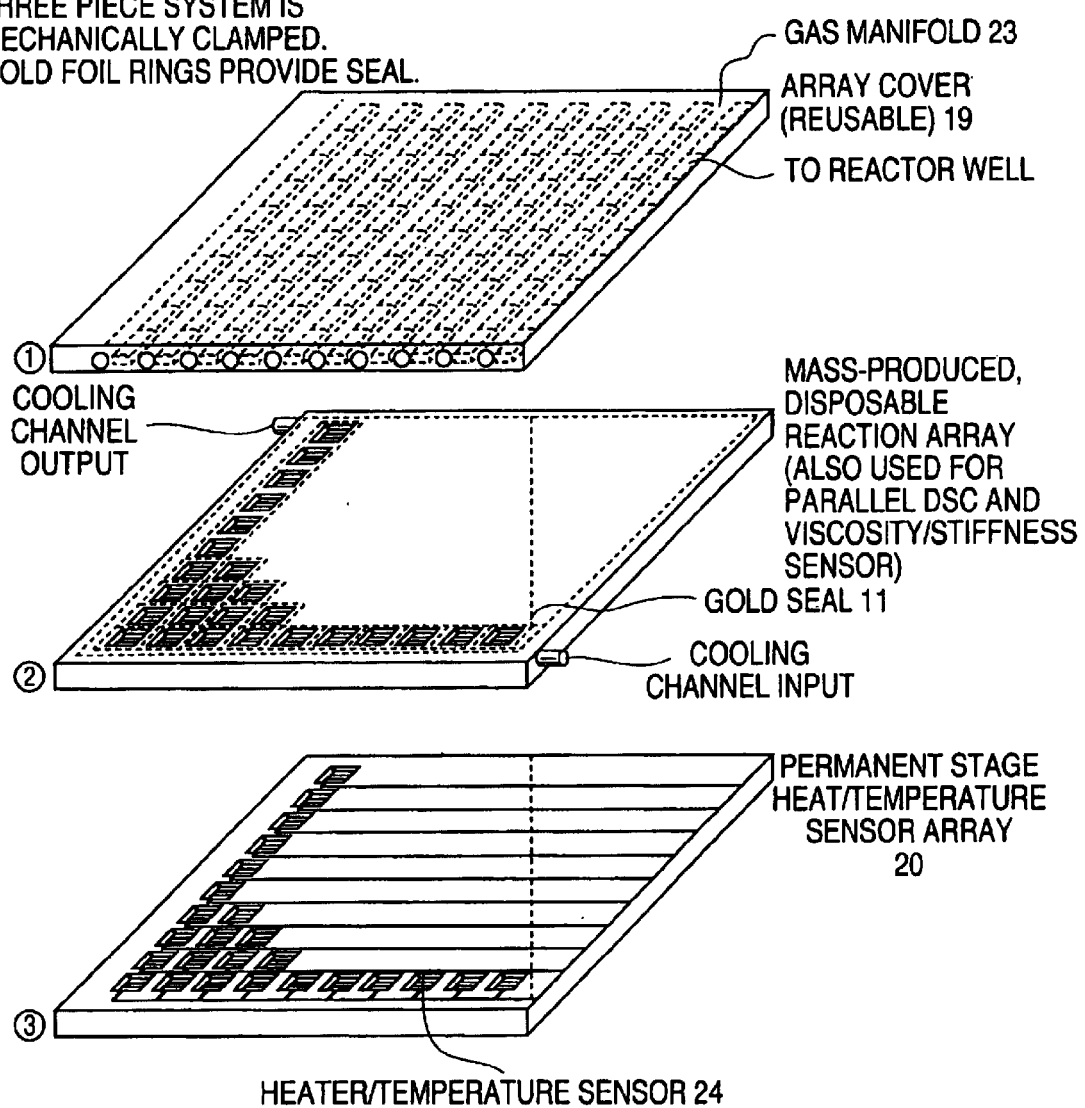

FIG. 11 shows an embodiment of the reaction calorimeter. The reaction calorimeter is composed of three sections, which may be mechanically clamped together. The array cover (19) comprises an array of gas manifolds (23), which are positioned over individual wells. In this embodiment, the array comprises cooling channels (8), and gasket/gold seals (11) disposed around the edges of each well. The wells further comprise a membrane layer forming the bottom of the well, and in direct contact with the stage (20). The stage comprises an array of heaters/temperature sensors (24), corresponding to the wells. The apparatus further comprises means, positioned over the array cover, for monitoring thermal changes from at least one well.

Figure 12:
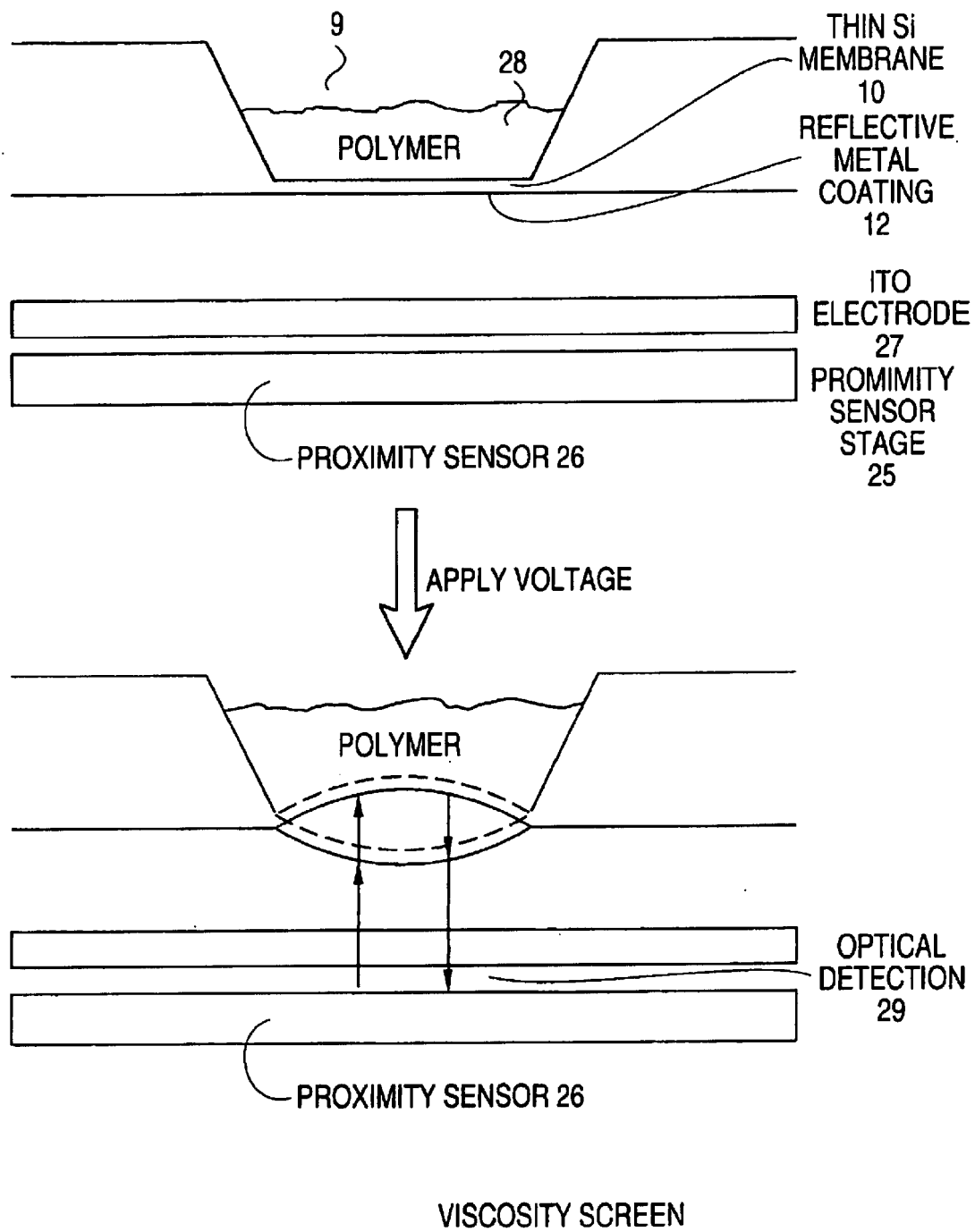

A cross section of an embodiment of the viscosity/stiffness sensor is shown in FIG. 12. The stage (25) is a proximity sensor stage, comprising a fiber optic detector, which is capable of optical detection (29). An indium tin oxide (ITO) electrode (27) is used to apply alternating electrostatic potential to induce vibration of the membrane(s). As shown in FIG. 12, the sample (28) is contained in a well (9), and the bottom of the well comprises a thin silicon membrane (10) comprising a thin, reflective metal coating (12).

Figure 13:
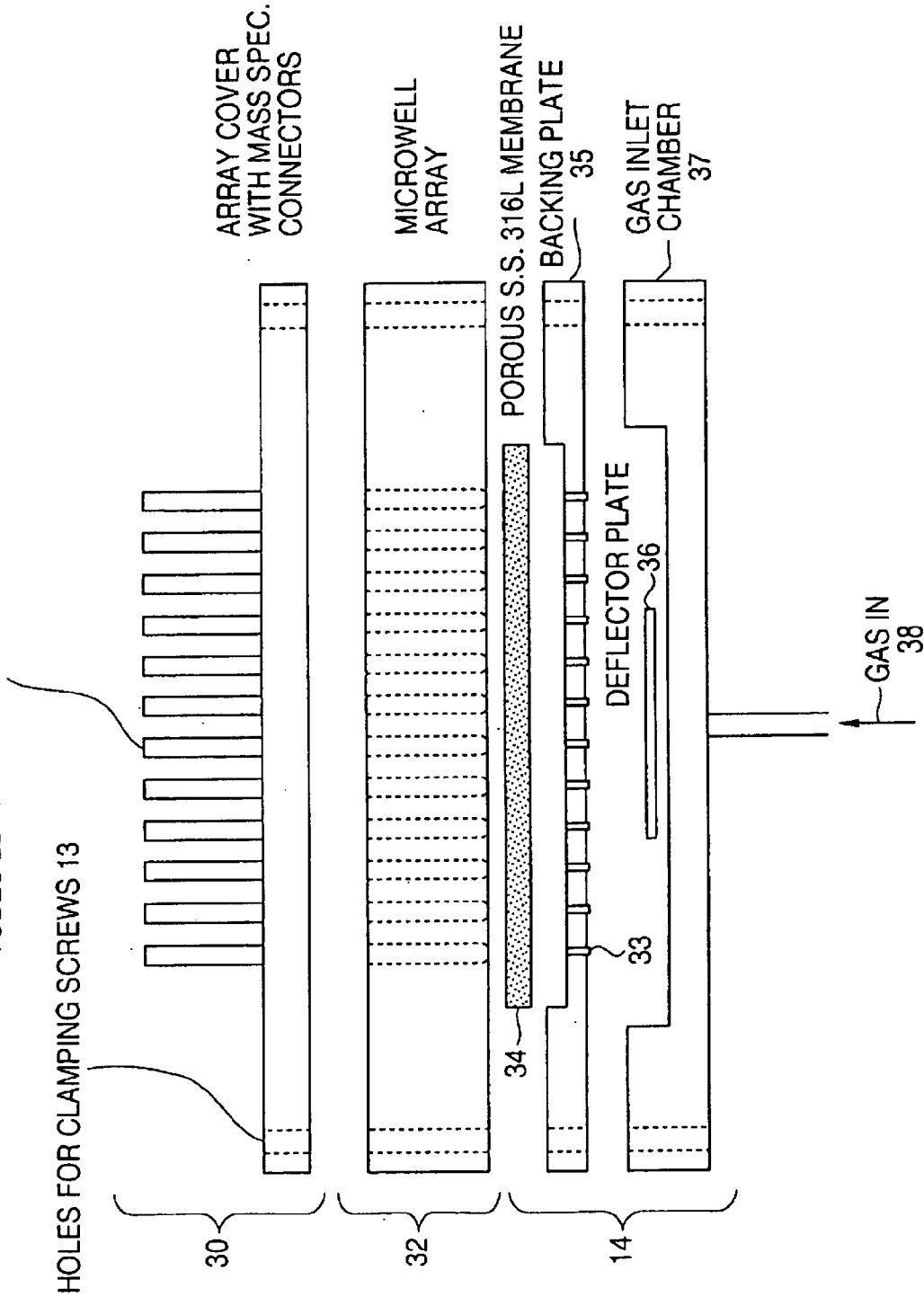

FIG. 13 shows a mass spectrometry apparatus comprising an array cover (30), an array (32), a stage (14), a mass spectrometer, and means for heating the samples in one or more wells. The array cover (30) comprises a gas manifold, which is in flow communication with the mass spectrometer. As shown in FIG. 13, the stage (14) comprises a porous stainless steel 316L membrane (34), a backing plate (35), a deflector plate (36), a gas inlet chamber (37), and a gas inlet (38). The array (32) is in contact with the stage (14), and the stage provides a heat source to the wells of the array. The array cover comprises tubes (31) leading to sampling valves which allow the products from selected microwells to be examined by the mass spectrometer.

Figure 7:
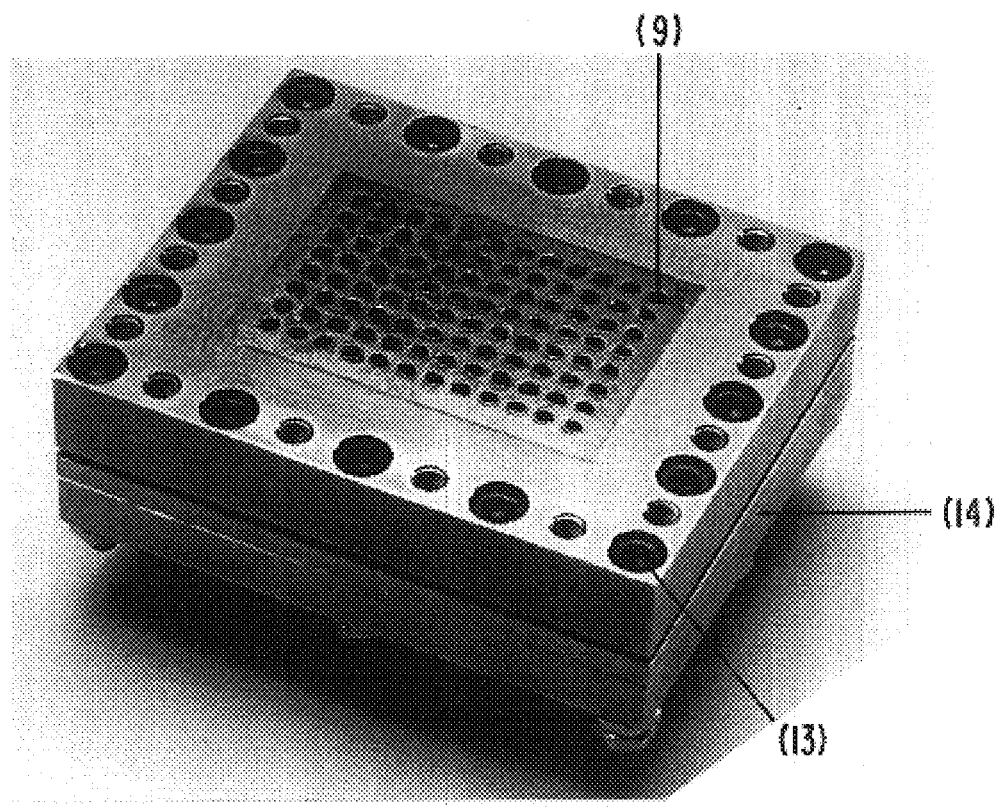
FIG. 7 shows an apparatus according to an embodiment of the invention, comprising an array having a plurality of wells (9) and a stage (14), where the stage may further comprises a gas manifold and/or means for regulating temperature or heating. Also shown are a series of holes (13) for attaching the array in an apparatus.
Figure 14:
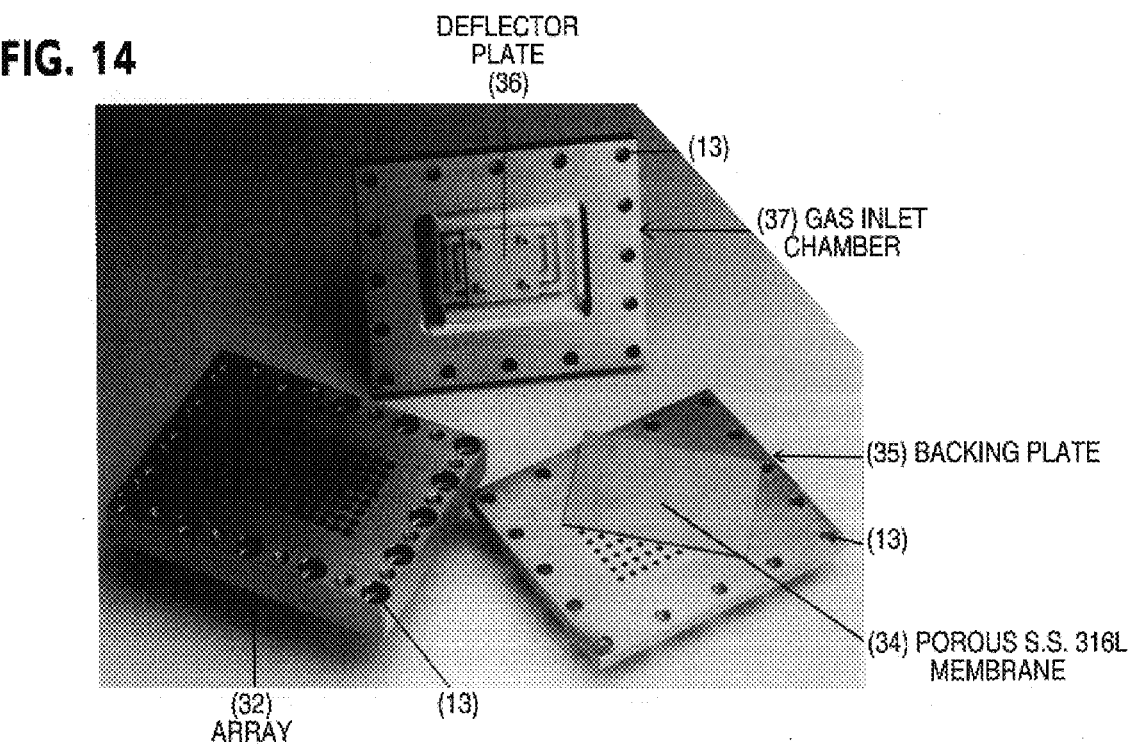
Figure 15:
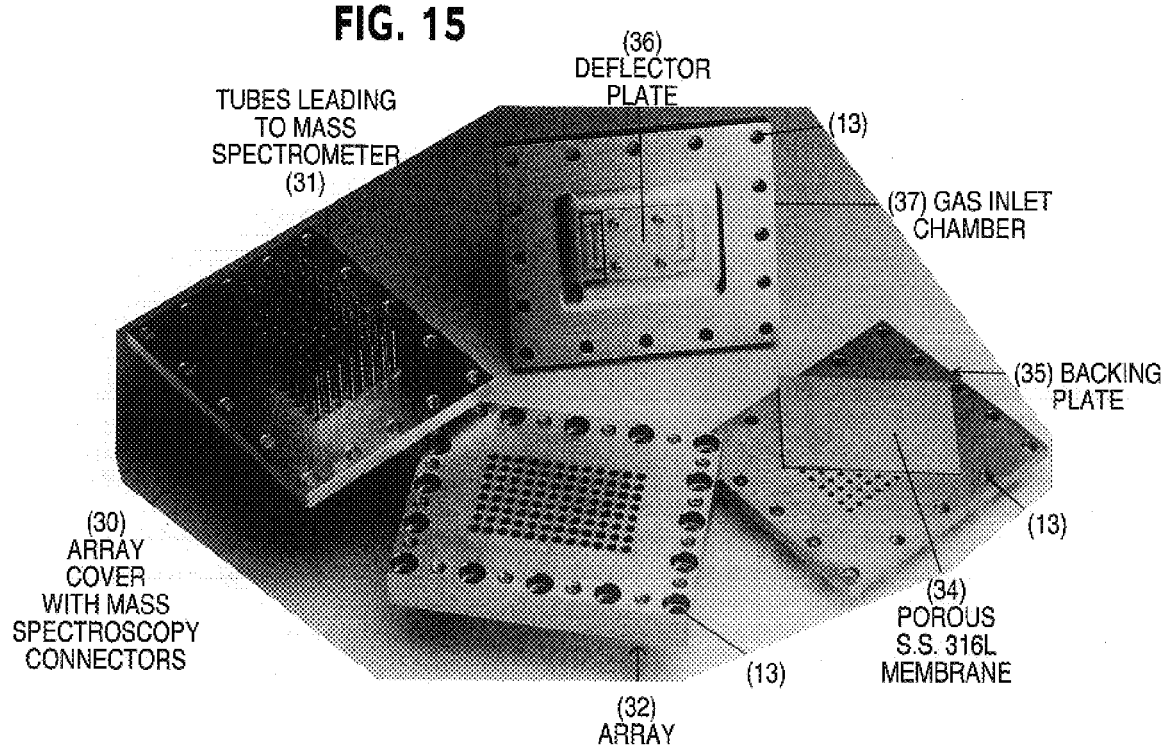

FIG. 14 and FIG. 15 show further views of an embodiment of the invention. Also FIG. 7 shows an embodiment of the invention where the array (32) and stage (14) are assembled, without the array cover.

Figure 16:
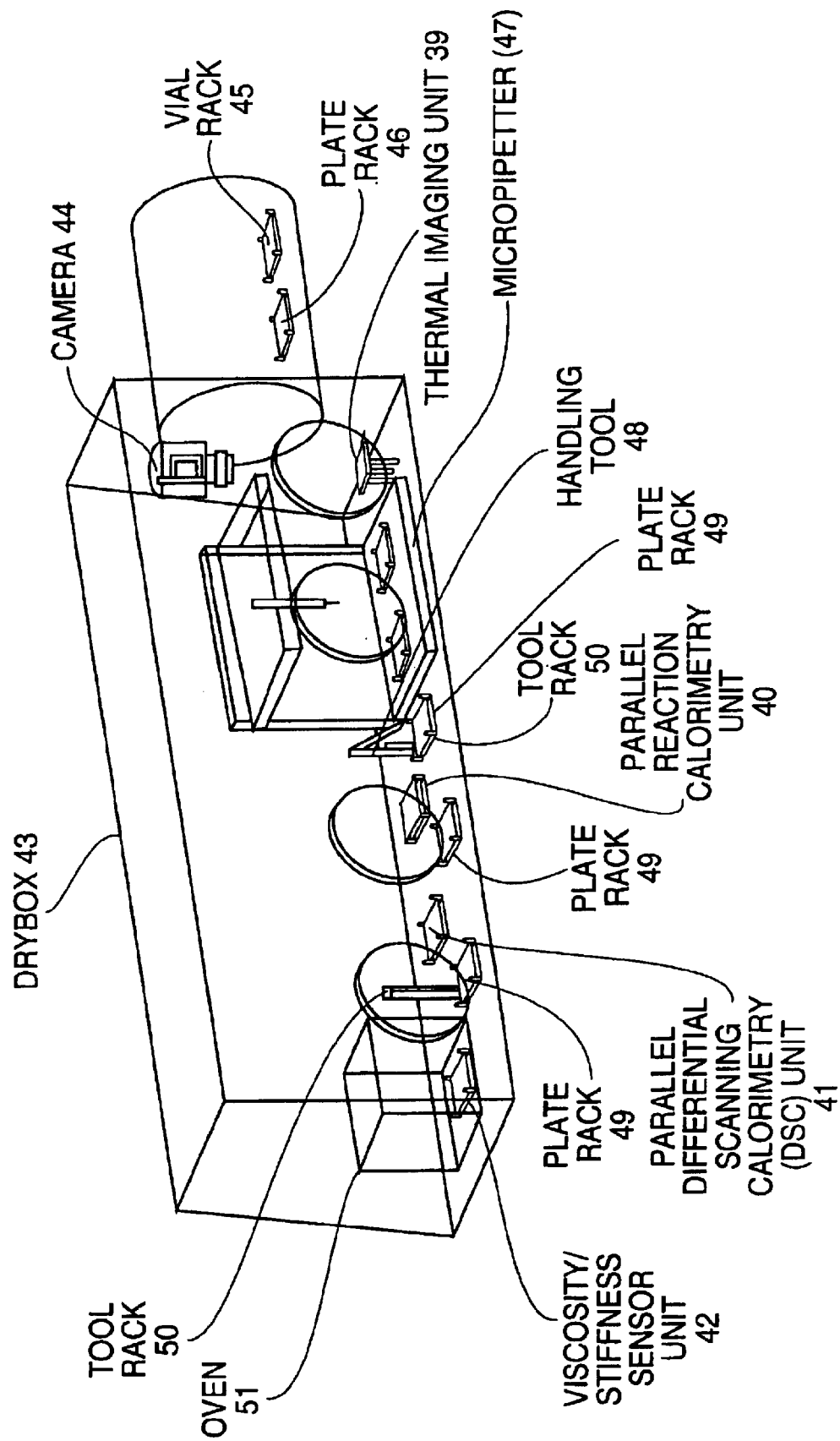

An embodiment of the workstation is shown in FIG. 16. The workstation incorporates a thermal imaging unit (39), a camera (44), a parallel reaction calorimeter unit (40), a parallel differential scanning calorimetry unit (41), a viscosity/stiffness sensor (42), and an oven (51). Optionally, the workstation is housed in a drybox/glovebox (43), and may optionally provide an inert atmosphere. Optionally, the workstation further comprises means for transferring the array from the first analytical instrument to a second analytical instrument. As shown in FIG. 16, there may be vial rack (45), plate rack positioned outside the workstation (46), micropipetter (47), handling tool (48), plate rack positioned inside the workstation (49) and a tool rack (50) in this embodiment.

Figure 17:
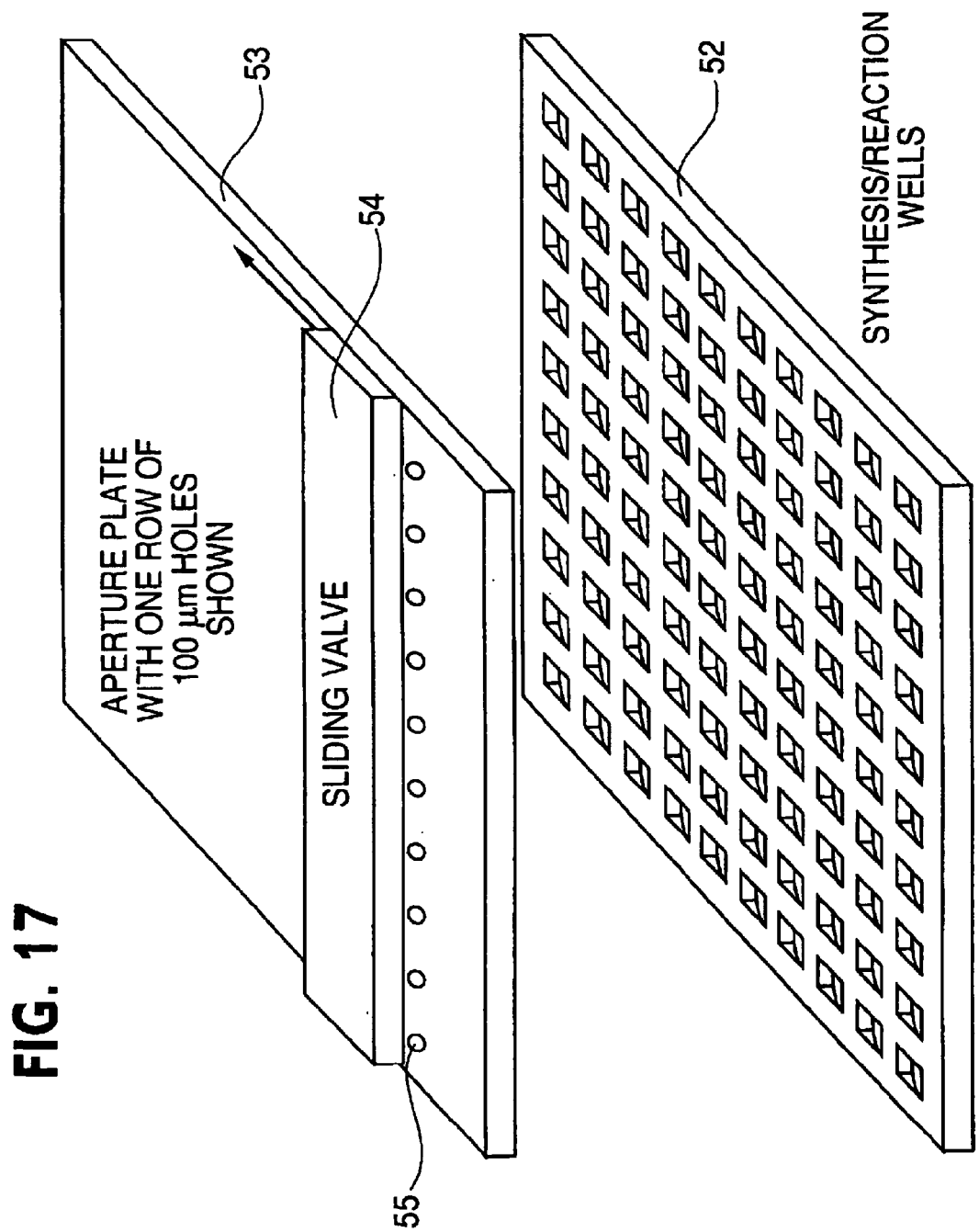

FIG. 17 shows an overview of the combinatorial reaction well and aperture plot.

Figure 18A:
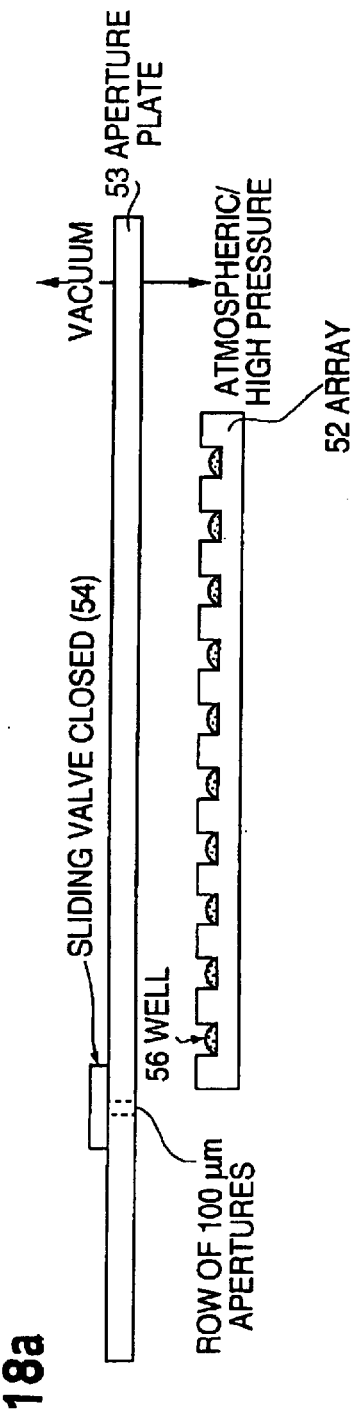
Figure 18B:
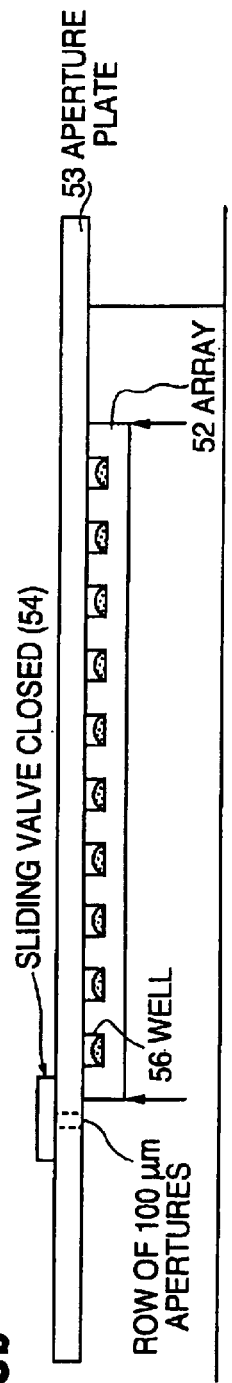
Figure 18C:
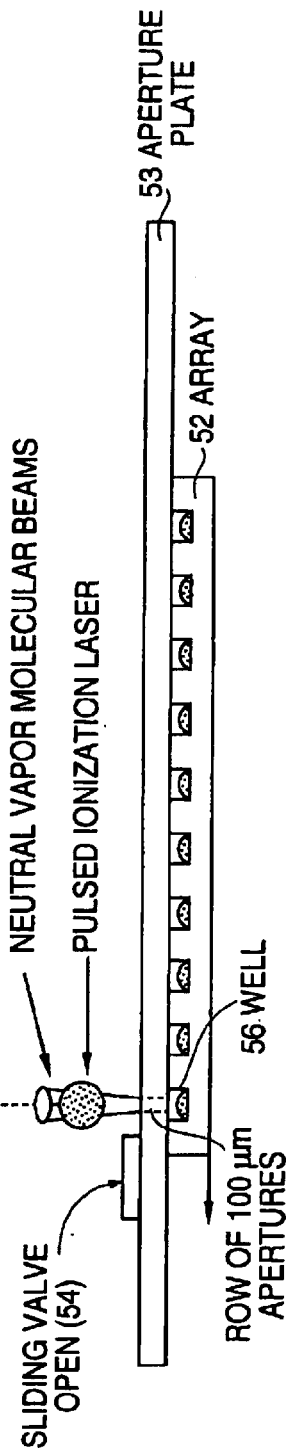

FIG. 18 shows a sequence of operations for gas phase analysis, including the Reactant Gas Dosing Phase (FIG. 18a), the Reaction Phase (FIG. 18b), and the Analysis Phase (FIG. 18c).

FIG. 19 shows the conceptual description of two-dimensional time-of-flight mass spectrometry.

FIG. 20a, FIG. 20b, FIG. 20c, and FIG. 20d show a possible instrument configuration for analysis of combinatorial reaction products.

Figure 21:
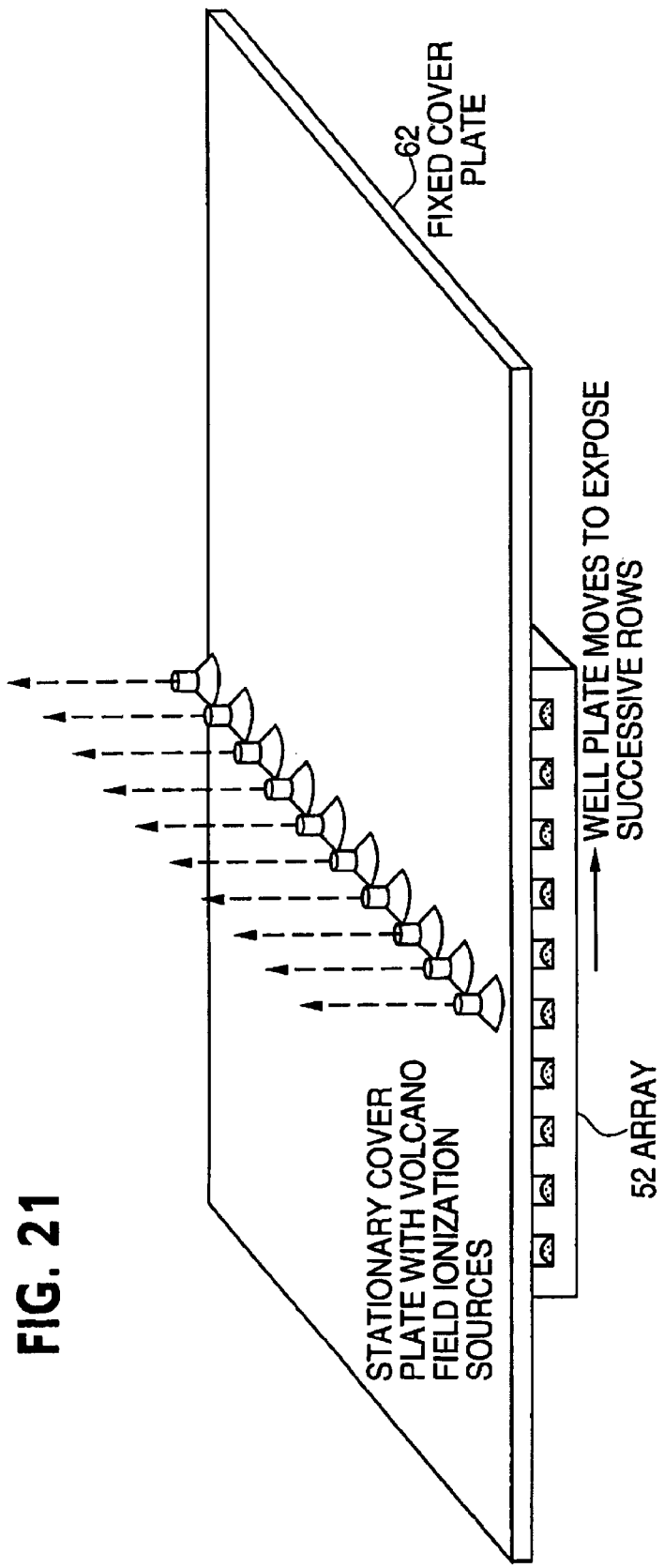

FIG. 21 shows alternative configuration for using volcano field ionization sources for organic/polymer analysis.

Figure 22:
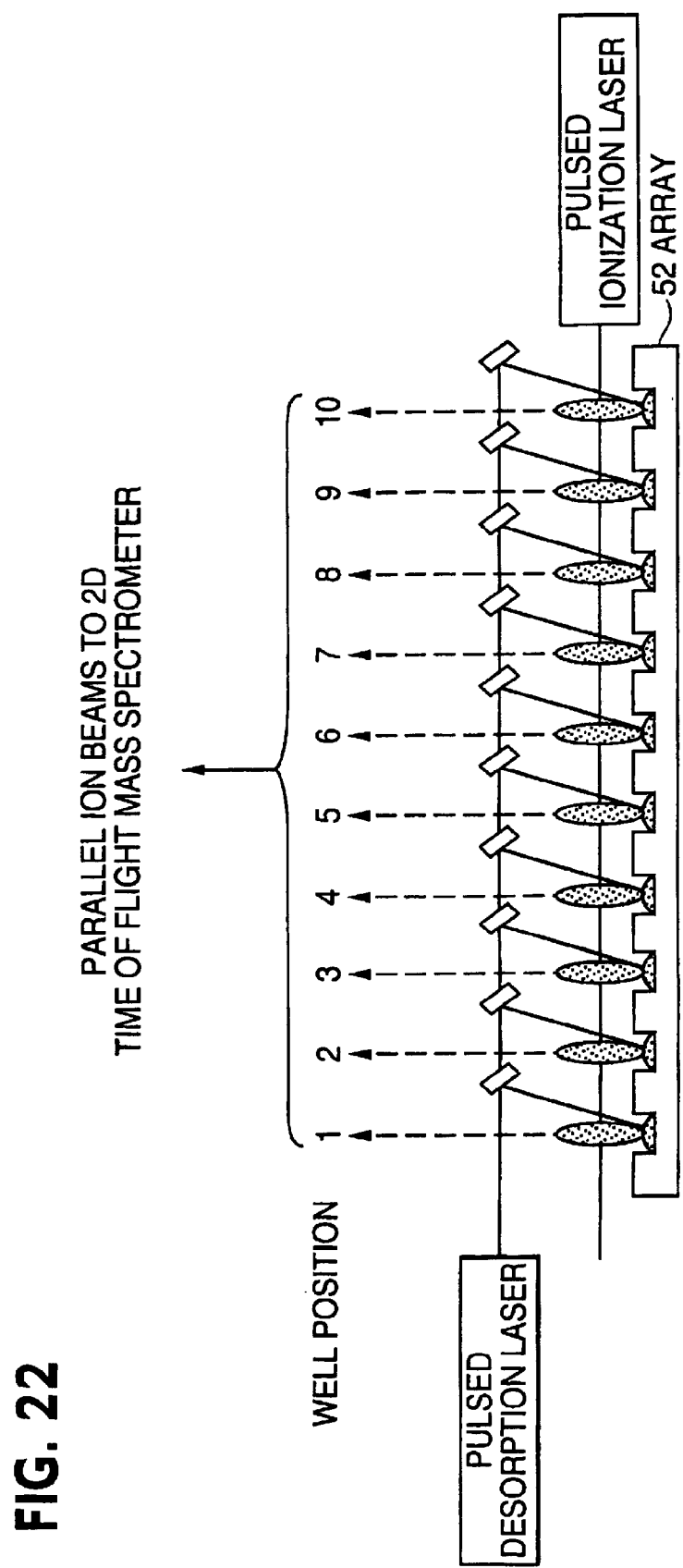

FIG. 22 shows a configuration for parallel bulk/surface composition analysis.

DETAILED DESCRIPTION OF THE PREFERRED EMBODIMENTS

I. Array

The invention relates to an array, which is used to generate combinatorial libraries of compounds. The array comprises a substrate having a plurality of wells. The substrate may be any material having a rigid or semi-rigid surface, and may be in any shape that is convenient and practical. The wells and thermal channels may be in the form of dimples, wells, raised regions or etched trenches in the substrate. Typically array have rows and columns in arrangements of about 8×12, and multiples thereof (i.e. 16×24, 32×48, etc.), or arrays of about 10×10, and multiples thereof (i.e. 100×100, 1000×1000, etc.). Depending on the application, the wells may also be arranged in a circular arrangement.

Moreover, in a preferred embodiment, the array can be easily interchanged between different stations or analytical instruments without requiring transfer of compounds or components of the library from the array. This feature of the array reduces sample preparation and sample transfer steps.

In one embodiment of the invention, the array comprises a substrate having at least one thermal channel. In some embodiments of the invention, the thermal channels may be metalized for resistive heating, or doped with a material selected from the group consisting of boron, phosphorus, or arsenic, among others. In other embodiments of the invention, the thermal channels may contain a fluid or gas, which is used to regulate the temperature. Preferably, the thermal channels contain a coolant, such as nitrogen, air, water, methanol, hydrocarbons, or halogenated hydrocarbons, which permits the reactions within the wells to be run at a desired temperature. Thus, according to the invention, the reactions within each well can run under isothermal conditions. In addition, the thermal channels allow for analytical analysis to be conducted under isothermal conditions. In preferred embodiments, the thermal channels may be aligned parallel to at least one row or column, or may define a checkerboard pattern around the wells of the array.

In a second embodiment of the invention, the array has at least one well that comprises a membrane, forming the bottom of the well. The membrane is flexible, thermally conductive, or gas-permeable, and comprises at least one material selected from the group consisting of silicon, doped silicon, silicon dioxide, doped silicon dioxide, steel, sapphire, a glass material, a ceramic material, a plastic material, silicon nitride, silicon oxynitride, and mixtures thereof Often the membrane is of a substantially uniform thickness, i.e. from about 100 nm to about 1 mm, from about 1 μm to about 50 μm, or from about 1 μm to about 20 μm. The membrane may be used in a number of applications, including monitoring the temperature of the reaction and characterizing the product contained in the well.

In a third embodiment, the invention relates to an array, which has thermal channels, and where the wells of the array have a membrane layer, which is flexible, thermally conductive, and/or gas-permeable. According to this embodiment, the thermal channels and the membrane layer are as has been described above in other embodiments of the invention. Any features of the other embodiments may be incorporated either alone or in combination in this third embodiment.

The wells of the array can have a variety of shapes, as will be evident to one of ordinary skill in the art. For instance, possible shapes for the wells include any of the following: tapered rectangle, cylindrical, U-shaped, V-shaped, and rectangular. The different shapes can be easily produced using standard techniques known in the art. (See K. E. Petersen, "Silicon as a Mechanical Material," *Proc. IEEE*, 70(5): 420–457(1982), which is hereby incorporated in its entirety.)

In general, the array may be fabricated such that the wells have a volume from about 1 nL to about 500 µL, depending upon the choice of material, as will be evident to one of ordinary skill. With other materials, the volume of the well may be greater than 1 mL. However, it is also possible to adapt the array to the microscale. Advantages of the microscale include smaller reactor volume, lower costs for reagents and labor, and generally higher throughput. The wells can be fabricated to have a volume of less than about 1 µL. In particular, the array may comprise wells having a volume of from about 1 nL to about 500 µL, from about 0.1 µL to about 100 µL, or from about 0.25 µL to about 10 µL.

The array is fabricated from a substrate, typically comprising one or more materials selected from silicon, doped silicon, silicon dioxide, doped silicon dioxide, steel, sapphire, glass materials, ceramic materials and plastic materials. It is also possible to have an array comprising a hybrid substrate, with different sections made from different materials. For instance, it may be desirable to bond together a glass plate having wells and channels machined and/or etched therein, with a silicon wafer that forms the bottom of the wells. Other acceptable materials will be evident to one of ordinary skill in the art.

For instance, acceptable materials for the array also include a variety of materials, such as but not limited to: Pyrex, quartz, resins, carbon, metals, or inorganic crystals. In particular, suitable materials for the array include steel and steel alloys, including materials such as stainless steel. A variety of ceramic materials, such as silicon nitride, silicon oxynitride, aluminum nitride, boron nitride, aluminum oxide, zirconium oxide, silicon carbide, lithium aluminum silicate and mixtures thereof may also be used. Several plastic materials are also well suited for the fabrication of the array. Typical plastic materials comprise at least one of polyethylene, polypropylene, polystyrene, polycarbonates, polyimides, poly(vinyl chloride), fluorinated polymers (for example, such as tetrafluoroethylene fluorocarbon polymers and fluorinated ethylene-propylene resins), acrylic, and poly (ethylene terephthalate). Other suitable materials will be apparent to one of ordinary skill in the art.

In one embodiment of this invention, a silicon wafer is used as the substrate for the array. This embodiment is preferred because silicon is relatively inexpensive and abundant, and available in high standards of purity. In addition, silicon-processing techniques are also easily amenable to miniaturization and have been well developed in related fields. Techniques have been developed to define and reproduce various device shapes and patterns using photolithographic techniques with high precision. (See K. E. Petersen, "Silicon as a Mechanical Material," *Proc. IEEE*, 70(5):420–457(1982), which is hereby incorporated in its entirety.) Moreover, arrays made from silicon wafers can be efficiently batch-fabricated.

Thus, the invention is able to take advantage of microfabrication technology, which provides a high degree of reproducibility and low-cost, batch manufacturing processes, to construct reactor well arrays from silicon wafers. For example, microfabrication technology provides a means to construct 100 virtually identical 8 µL microwells with thin membrane bottoms and a cooling system onto a single silicon wafer. These microreactors can be used to approximate the regulated conditions of bench-scale (or commercial) polymerizations. The flat silicon surface provides for an excellent seal to prevent well cross-contamination. The thin membranes provide for rapid heat transfer, enable calorimetry measurements, and provide the flexibility for viscosity/stiffness characterization. Thus, the melting points and viscosities of the resulting polymers within the reaction wells can be measured in the array. The arrays can be mass-produced at relatively low cost.

In cases where doped silicon or doped silicon dioxide are used, typical dopants include, but are not limited to, boron, phosphorus, and arsenic. The amount of dopant used is an amount from about $10^{13}$ atoms/cm$^3$ to about $10^{19}$ atoms/cm$^3$, from about $10^{14}$ atoms/cm$^3$ to about $10^{17}$ atoms/cm$^3$, or from about $10^{15}$ atoms/cm$^3$ to about $10^{16}$ atoms/cm$^3$. Other appropriate dopant materials and concentrations of the dopant will be evident to one skilled in the art, and is selected appropriately, depending upon the particular embodiment and application of the invention.

When the array is made from a silicon wafer, the array has the additional feature and advantage of being well adapted for single-use applications. In particular, the array may be disposable or archivable. By batch-fabricating the array, the array may be produced at a cost such that it is cost-effective to dispose of the array after use, which avoids time-consuming cleaning operations and the risk of contamination. Alternatively, the array may be archived. In this instance, it may be desirable to use an array cover to seal the array under vacuum or provide an inert atmosphere prior to storage. Archiving the libraries permits easy access to compounds for future studies or characterization.

Fabrication of Array With Thermal Channels From Silicon

In one embodiment of the invention, the array is fabricated from a wafer, such as a silicon wafer. The term wafer includes a thin, round slice of a semiconductor material, usually comprising silicon. The wafer will typically be processed through a series of steps, where it is ground to have a smooth, polished surface. Silicon wafers are commercially available in a variety of forms, purity, and compositions. Such silicon wafers are commercially available from a variety of commercial sources, such as International Wafer Service, Portola Valley, Calif.

Figure 1:
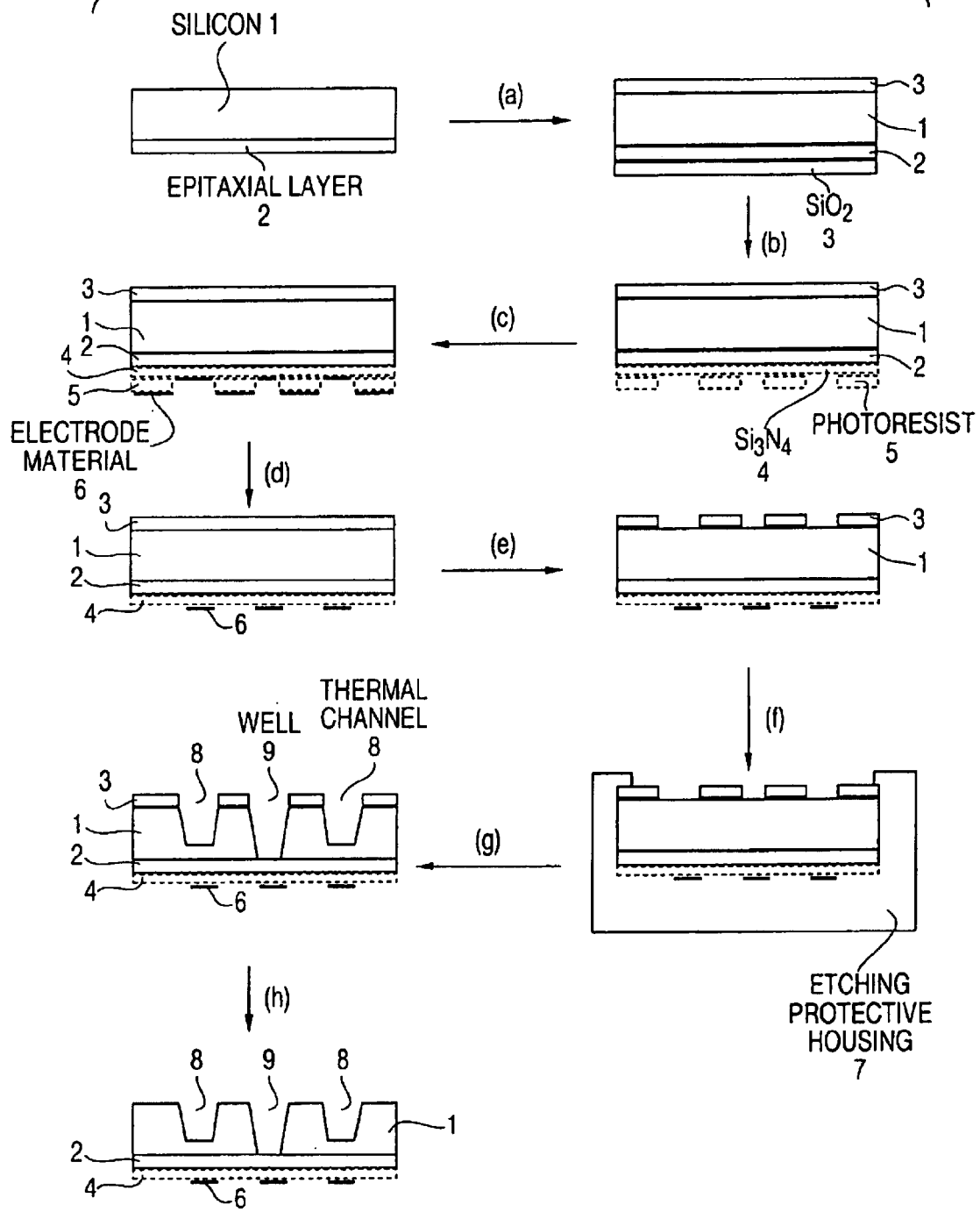

This process is shown in FIG. 1. Typically, a lightly doped (100) silicon wafer (1) is used. However, the amount of dopant in the wafer may vary depending on the etching method used, as will be apparent to one of ordinary skill in the art. In general, atoms with one less electron than silicon (such as boron), or one more electron than silicon (such as phosphorus) are introduced into the area exposed by the etch process to alter the electrical character of the silicon. These areas are referred to as P-type (boron) or N-type (phosphorus) to reflect their conducting characteristics. In particular, it may be desirable to selectively dope a portion of the wafer in order to control the rate of etching, during the fabrication of the array.

Wafers are usually fabricated in a clean, dust-free room. The first step may be a pre-cleaning step using high purity, low particle chemicals. An epitaxial Layer (2) may be grown, and/or the silicon wafers may be heated or exposed to ultra-pure oxygen in the diffusion furnaces under controlled conditions to form a silicon dioxide film (3) on the surface of the wafer. This film will preferably have a substantially uniform thickness on the wafer from about 0.8 about 1 micrometer thick. Alternative masking materials such as silicon nitride (4), may also be used.

Masking is a procedure for protecting one area of the wafer, while working on another. This procedure is also known as photolithography or photo-masking. Masking comprises a step of applying a photoresist (5) or light-sensitive film to the wafer, giving it characteristics similar to a piece of photographic paper. A photo aligner is used to align the wafer to a mask. Then intense light is projected through the mask and through a series of reducing lenses, exposing the photoresist with the mask pattern. Usually, the wafer and the mask are aligned precisely prior to exposure. Preferably, the alignment tools used are fully automated.

The exposed photoresist is removed, and the wafer is baked to harden the remaining photoresist pattern. The wafer is then exposed to a chemical solution or plasma (gas discharge) so that the silicon dioxide areas not covered by the hardened photoresist are etched away. Finally, the photoresist is removed using additional chemicals or plasma. Optionally, an electrode material (6) may be deposited using a similar masking procedure.

The wells (9) and cooling channels (8) of the array are typically formed by etching the silicon, while placing the wafer in an etching protective housing (7) to protect the other side of the wafer. Various etching methods are used, including but not limited to wet etching methods. If wet etching methods are used, etching agents such as potassium hydroxide (KOH) or ethlylene diamine pyrocatechol (EDP) are used. Once the silicon etching rate for a particular etching agent at a certain temperature is determined, the depth of the well (9) and thermal channels (8) can be controlled by controlling the etching time. Typical silicon etching rates are known in the art, and available in a number of handbooks. See K. Petersen, "Silicon as a mechanical material," Proc. IEE, 70(5):420–457, 1982, which is hereby incorporated in its entirety In order to control the depth of the wells more precisely or to create a membrane layer (10) forming the bottom of the well, the etch-stop method is often used. There are several ways to stop etching at a certain cavity depth so as to form a membrane. In one instance, the membrane section of the silicon substrate is heavily doped by boron. The doped section of the silicon substrate will not be substantially etched, or is only slowly etched in EDP etching solution. Alternatively, the electrochemical technique is used. In this case, the membrane section is doped such that a lightly doped p-n junction is formed between the membrane section and the other section to be removed. A bias is applied during the wet-etching between the two section to stop etching in the membrane. For both boron etching stop or electrochemical etching methods, the membrane section is formed by diffusion of dopant from the silicon surface or by the epitaxial growth of a silicon thin film.

A third etching stop method is to use a buried oxide layer, called silicon on insulator (SOI). A thin silicon dioxide layer is formed between the membrane and bulk sections and used as an etching-stop layer. The silicon on insulator structure is made by bonding two silicon wafers, one having a silicon dioxide layer on the surface, and grinding the other silicon wafer to a desired membrane thickness.

The thermal channels (8) are also made by etching techniques. Typically, a V-groove shape is made, and the array is then mechanically clamped with an array cover having a metal gasket to form a thermal channel. For example, a cooling medium may flow through these channels. A metal inlet is placed in the channel entry.

After forming the wells (9) and thermal channels (8), the silicon dioxide layer is removed. If desired, gaskets can be applied around each well, usually by depositing a thin film around the edges of the wells in the array by a combination of photolithography and thin film coating methods (i.e. evaporation or sputtering). Typical materials used for the gasket include gold and copper. The film can be further thickened by electroplating after completing the well and cooling channels. Graphite and polymers are also useful gasket materials, although these are typically used as 0-rings or on a sheet patterned to match the array, which is laid on the array, rather than being microdeposited on the array.

Figure 2:
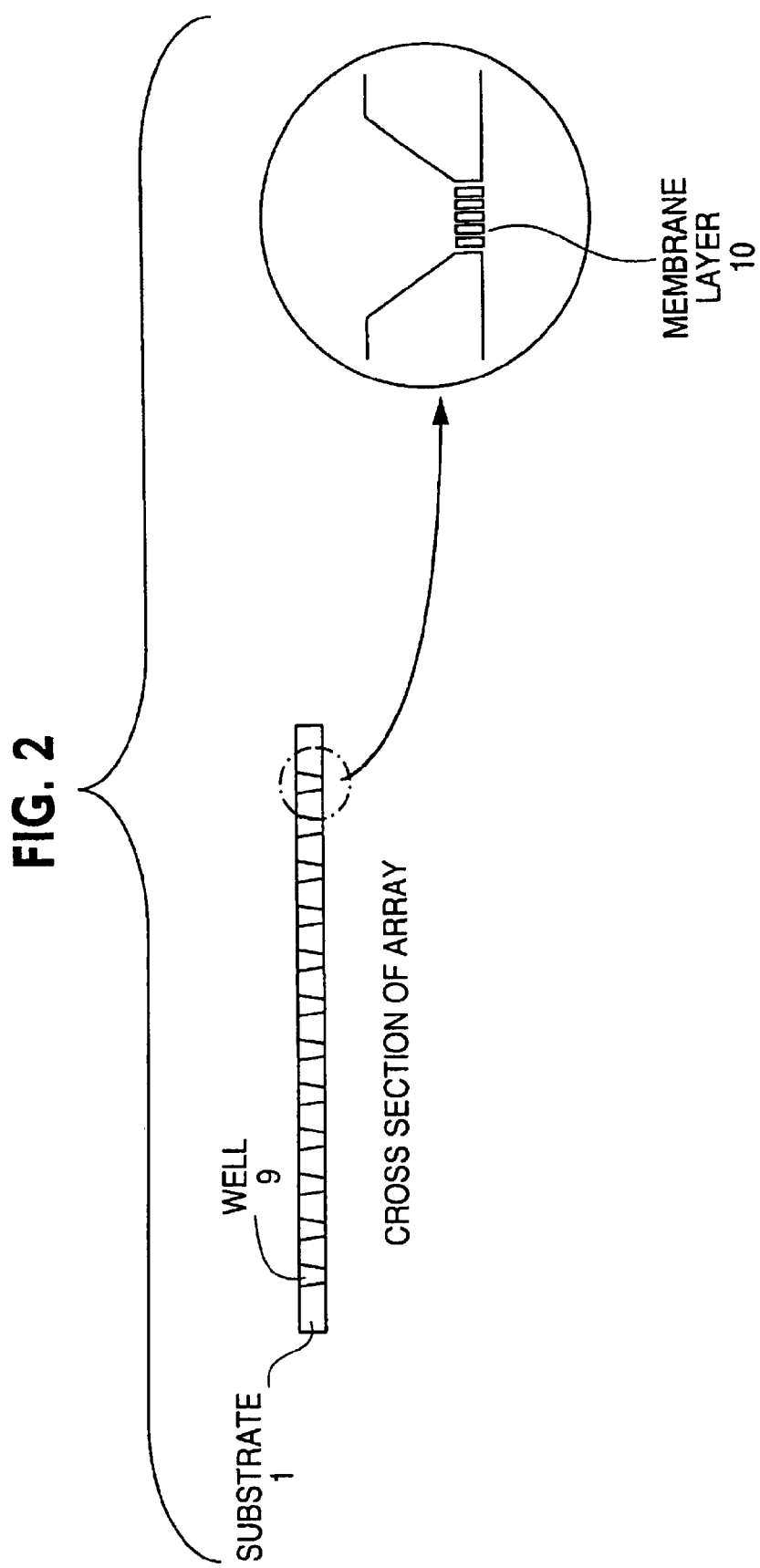
Figure 3:
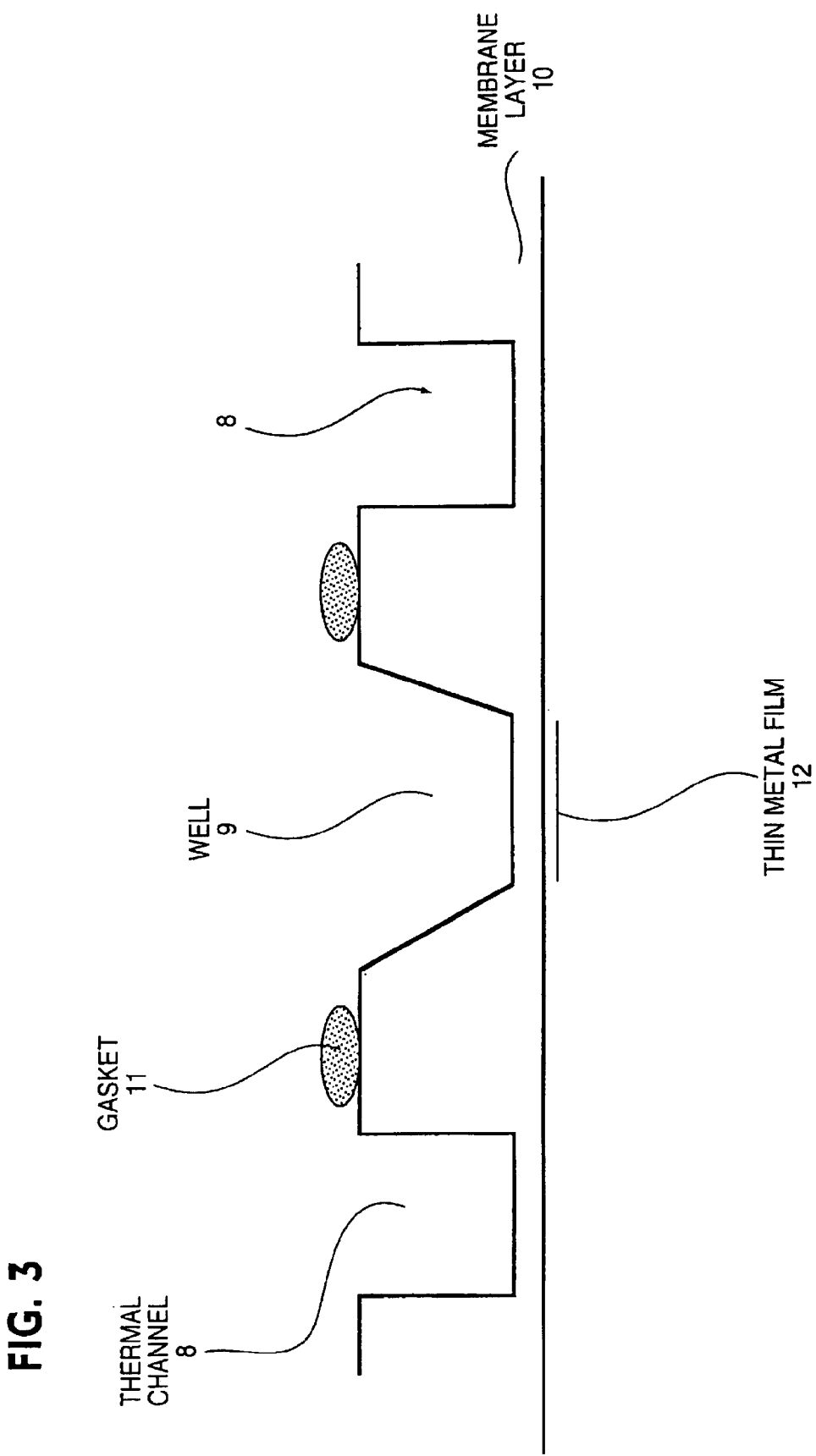

A cross-section of the array is shown in FIG. 2 and FIG. 3. In these figures, the well (9) and thermal channels (8) are shown. The gasket (11) is also shown, as well as the location of the membrane layer (10). In some embodiments, a thin metal film (12) will also be present at the bottom of the well.

FIG. 2 and FIG. 3 show a cross section of an embodiment of the array. A magnification of the membrane layer, showing the porosity is shown in detail in FIG. 5A, FIG. 5B, FIG. 6A, and FIG. 6B.

Figure 4:
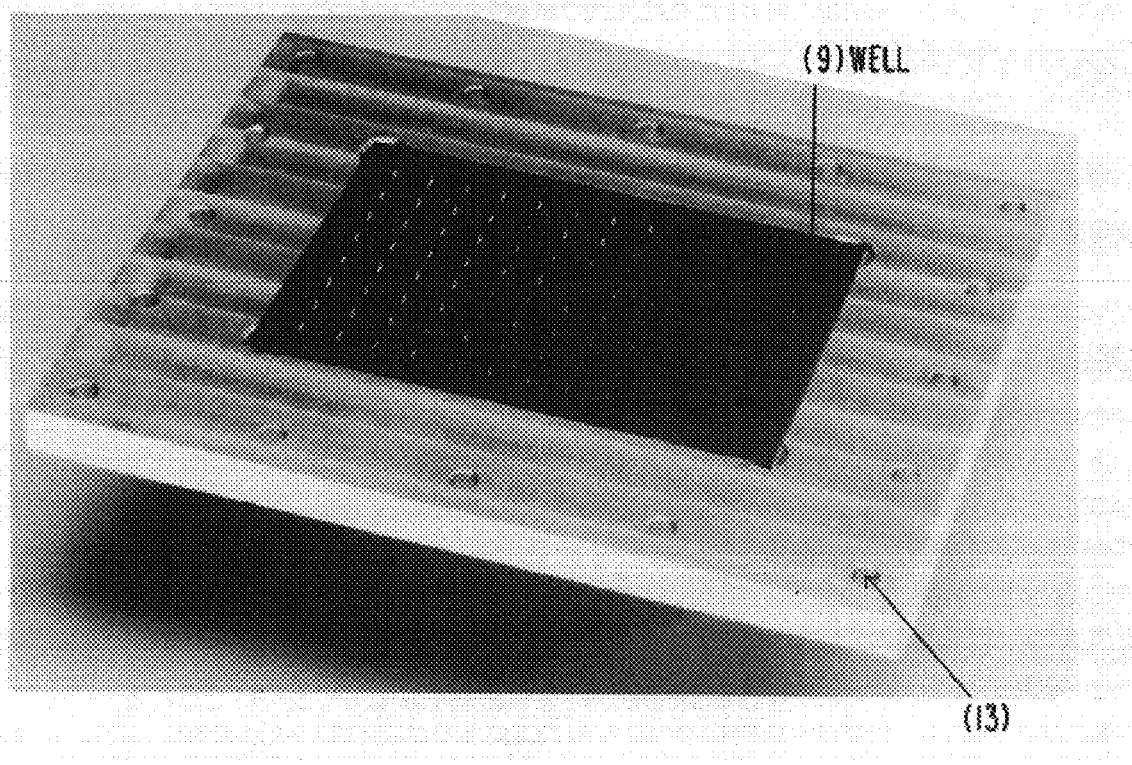

Fabrication of Array From Stainless Steel, Ceramic Plastic, or Other Machinable Material The array can also be made from other machinable materials such as stainless steel, ceramics, or plastics. FIG. 4 shows an embodiment of the invention, where the array was made from stainless steel. The choice of material depends on the compatibility of the reactants with the material and the temperature regime used. Typically stainless steel is a convenient choice, with 316 alloys being preferred. Other alloys such as HASTOLY™ or INCONEL™ may be preferred for corrosion resistance with halides. HASTOLY™ is a family of high-strength, nickel-based alloys with a high resistance to uniform corrosion and stress, while maintaining ease of welding and fabrication. HASTOLY™ is commercially available from sources such as Haynes, Kokomo, Ind. INCONEL™ is the name for a series of corrosion-resistant alloys of nickel and chromium, and is commercially available from sources such as Inco, Huntington, W.Va. Ceramic materials such as alumina or silicon nitride or silicon carbide may also be used. Once machined, these materials can also be coated with inert material such as silica or metals such as gold for further corrosion resistance.

In one embodiment, the invention relates to an array made from stainless steel. In this embodiment, a 3 ⅛ inch ×3 ⅞ inch ×⅝ inch thick stainless steel block, was drilled to produce 96 wells, where the wells had a diameter of 3 mm, were drilled in an area of 1 ½×2 ⅛ inches, and formed by drilling an 8×12 grid of holes 3 mm in diameter. The dimensions of the holes and the height of the reactor can be modified for smaller or larger wells. Typical dimensions for the wells in an array comprising stainless steel may range from 0.1 microliter to 1 mL, 5 microliter to 500 microliter, and/or 25 microliter to 100 microliter. In this particular example, the holes taper at the bottom of the array to lead to 1 mm diameter holes at the bottom. The spacing of the holes is such that they are compatible to conventional pipeters and combinatorial work stations. In this example, the holes are spaced 4.5 mm apart. A second block of stainless steel, of similar length and depth and corresponding holes is also used as a backing plate. In this embodiment, the hole size was 2 mm in diameter, although the hole size may be even smaller. In this embodiment the thickness was ¼ inch, although the thickness can be even less. Depending on the size of the array, the thermal channels may be made by conventional drilling techniques, as will be evident to one of ordinary skill in the art.

A porous membrane such as a stainless steel mesh of 0.1 to 2 micron porosity is placed between the array module and backing module. Gaskets, consisting of a soft material, such as carbon, can be placed between the modules to insure no leakage between the modules. A third module is made of similar exterior dimensions to fit underneath the backing plate. This module has a hole or holes drilled through it to allow gases to flow into the array. One side is hollowed out and a plate is fabricated over the gas flow hole to distribute the gases evenly throughout the array. All modules are polished smooth by common machining practices to assure a good fit when assembled. Screw holes are placed on the edges of all the modules so that the modules can be bolted together to form the microreactor assembly. Additional mounting holes are drilled and tapped on the top module so that an analysis module can be attached.

Fabrication of Array With Wells Having a Flexible, Thermally Conductive, or Reflective Membrane Layer In another embodiment, the array has wells having a flexible, thermally conductive, gas-permeable, and/or reflective membrane layer. The membrane may be useful for a number of different types of analysis techniques, i.e. by measuring the response time of the membrane to such stimuli as electromagnetic vibrations or heat transfer, for example. FIG. 2 and FIG. 3 show a cross section of an embodiment of the array. A magnification of the membrane layer, showing the porosity is shown in detail in FIG. 5A, FIG. 5B, FIG. 6A, and FIG. 6B.

Such arrays may be fabricated from a material such as a silicon wafer. In one embodiment, this process is substantially as shown in FIG. 1, except that instead of an electrode layer, a variety of materials may be used, or in an embodiment of the invention, the electrode layer may be optional. A double side polished silicon wafer is used. Doping is controlled during the growth of silicon large boules, which can then be sliced into wafers. Doping levels are measured by the resistivity and the desired level is smaller than about 100 ohm-cm. The silicon wafers are commercially available, from a variety of commercial sources, such as International Wafer Service, Portola Valley, Calif.

For example, a square shaped well having a 5 mm by 5 mm entrance is made on the silicon wafer by the etching techniques described previously. A number of chemical etchants for silicon are well known. See K. Petersen, "Silicon as a mechanical material," Proc. IEE, 70(5):420–457, 1982, which is hereby incorporated in its entirety. Typically, an etchant such as potassium hydroxide (KOH) is used.

The bottom of the well is a thin membrane, formed by the following steps: producing an etch-stop layer, depositing a thin metal film or electrode layer, and etching the wells. The first step, the etch-stop step, is used to produce a uniform membrane thickness with good precision. The KOH etching agent exhibits reduced etch rates on silicon heavily doped with boron. Therefore, the part of the substrate that is to become the membrane layer is selectively doped with boron. One way to selectively dope part of the substrate is to grow a boron doped layer on the silicon, forming an epitaxial layer (2). The thickness of the epitaxial layer will determine the thickness of the membrane. The eptitaxial process is further described in K. Petersen, "Silicon as a mechanical material," Proc. IEE, 70(5):420–457, 1982, which is hereby incorporated in its entirety.

The etch-stop method has the drawback that the boron doped silicon is etched very slowly in KOH. An alternative technique is to use a buried silicon dioxide layer, which is also known as silicon on insulator (SOI). According to this technique, the buried silicon dioxide is made by bonding two silicon wafers together, one of which has a silicon dioxide layer on the surface, followed by grinding the silicon part until the desired silicon thickness is obtained. This process is further described in K. Petersen, "Silicon as a mechanical material," Proc. IEE, 70(5):420–457, 1982, which is hereby incorporated in its entirety.

After the etch step, a silicon dioxide layer (3) which is about 1 micrometer thick is thermally grown on the surface, or formed by exposing the wafer to ultra-pure oxygen in a diffusion furnace under controlled conditions. The photoresist (5) is coated on the membrane side and a resist pattern is made by the photolithography process. A metal film (6) is deposited on the membrane side of the silicon wafer that has the resist pattern, and then the resist is removed. This process, called the lift-off process, produces a metal film (6) or electrode material in the area where resist does not occupy.

In an embodiment of the invention, the wells do not have a flexible, thermally conductive or reflective membrane layer. The array is made in substantially the same manner as described above, but the electrode formation process is omitted.

Next, a photoresist pattern is formed on the oxide layer of the well entrance side. The oxide layer is etched using the etching solution. The membrane side not being etched is protected by either coating with a very thick photoresist or using a stainless steel housing (7) that is designed such that only one side of the wafer is exposed to the KOH solution. The silicon wafer is immersed into the etching solution. The solution temperature is 50° C. and the etching rate is about 1 micrometer per minute. This process is further described in K. Petersen, "Silicon as a Mechanical Material," Proc. IEE, 70(5):420–457, 1982, which is hereby incorporated in its entirety. In order to increase the etching rate, the temperature of the solution can be raised. For example, the etching rate is 1.4 micrometer per minute at 85° C. After forming the well (9), the protective silicon dioxide layer is removed in a dilute HF solution (approximately 6% in water). Alternative materials, such as silicon nitride, may also be used as the etching protective layer.

The thermal channels (8) are fabricated by the same masking and etching techniques described for making the well (9). The V-groove is formed and the cross section of the channel is determined by the width of the top opening area.

Figure 5A:
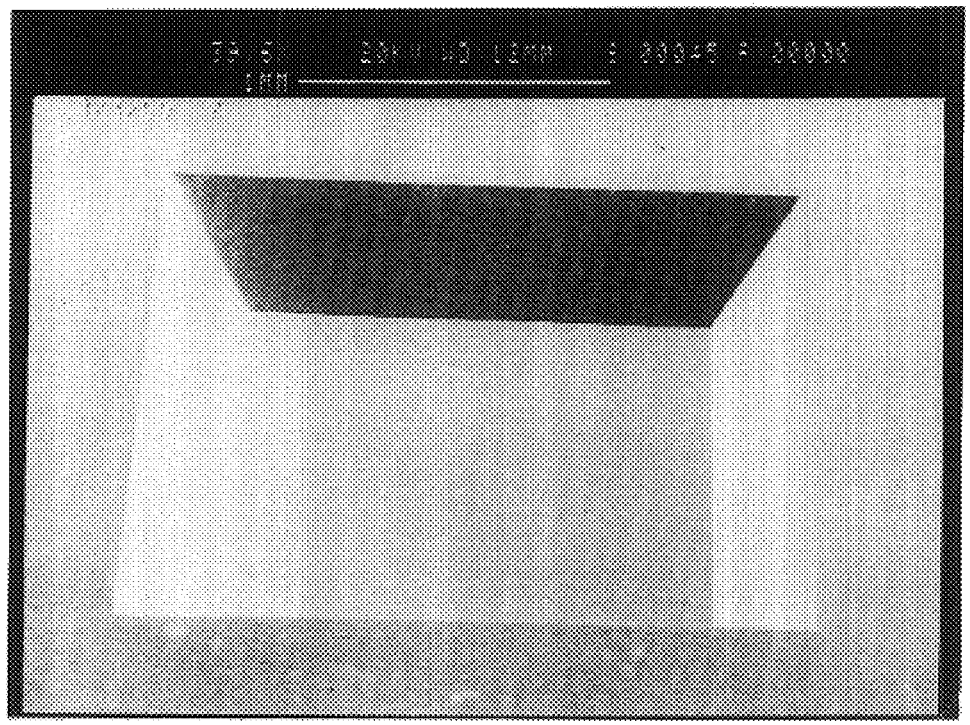
Figure 5B:
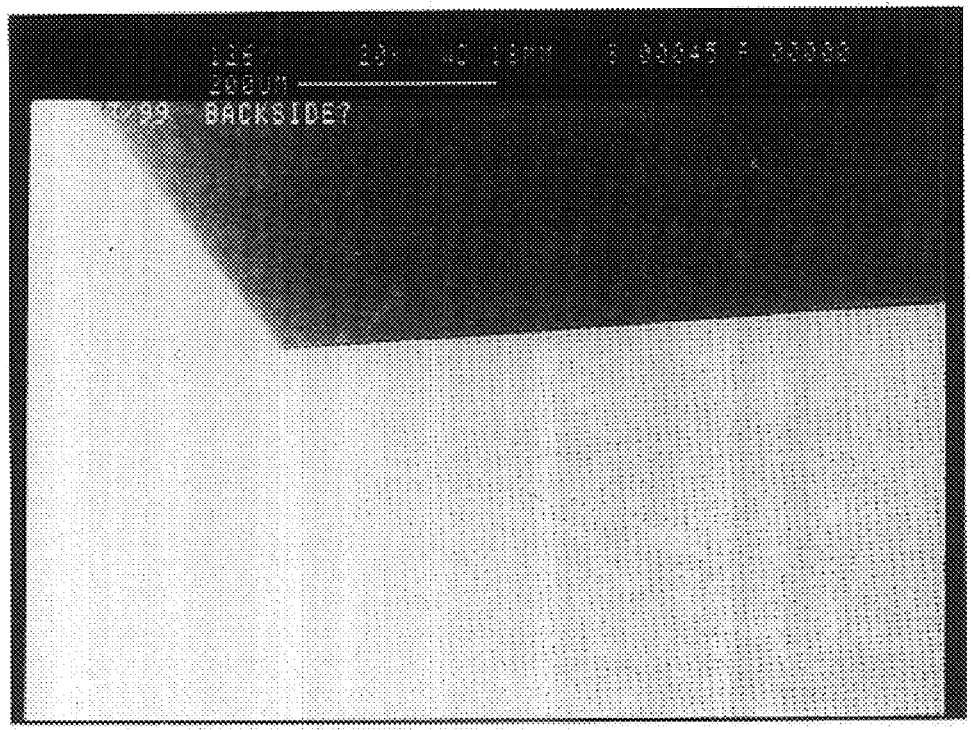

FIG. 5A and FIG. 5B show an embodiment of the array. A magnified view of the well (9) is shown in FIG. 5A. FIG. 5B shows a greater magnification of FIG. 5A, where the porosity of the membrane layer of the well is shown.

Figure 6A:
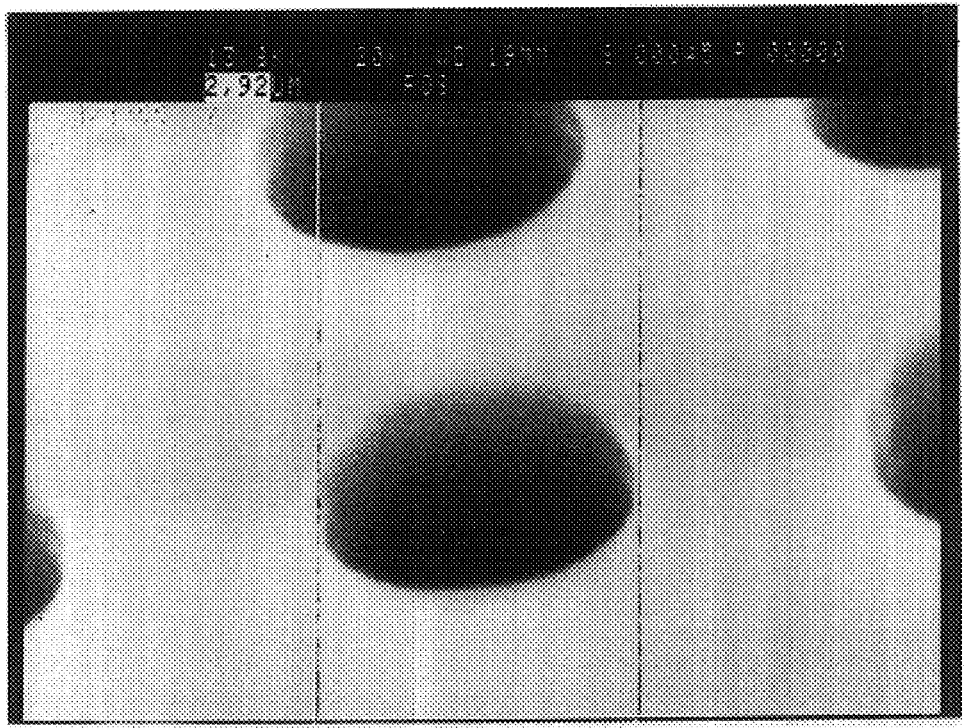
Figure 6B:

FIG. 6 is a magnification of the array shown in FIG. 5. FIG. 6A is a magnification of the view in FIG. 5B, where the porosity of the membrane layer is shown. FIG. 6B is a further magnification of FIG. 6A, where the porosity of the membrane layer is shown in greater detail.

Fabrication of Arrays Consisting of Silicon and Glass

When the array needs to be about 5 mm or thicker, the array can be made of silicon and glass. Wells and thermal channels are made on a glass plate by conventional machining, or "drilling". The glass plate is bonded to the silicon middle section by the anodic bonding method, which is further described in K. Petersen, "Silicon as a mechanical material," Proc. IEE, 70(5):420–457, 1982, and W. H. Ko, J. T. Suminto, and G. J. Yeh, "Bonding Techniques for Microsensors," in Microsensors, Ed. by R. S. Muller, R. T. Howe, S. D. Sendturia, R. L. Smith, and R. M. White, IEEE Press, 1991, page 198–208. These references are hereby incorporated in their entirety.

Covered Array

The covered array comprises an array, as has been described in detail above, and an array cover. In a second embodiment of the invention, the array will comprise thermal channels. In a third embodiment, the array will comprise wells having a membrane layer at the bottom of the wells in the array, and in another embodiment, the array will comprise thermal channels, and wells having a membrane layer at the bottom of the wells in the array. The array may also be adapted to the microscale. Any of the features of described for the array may be included, either taken alone or in combination.

The array cover may be further adapted depending upon the application. For example, the array may comprise either an individual gas manifold or an array of gas manifolds disposed over the wells and/or the thermal channels. The gas manifolds may correspond to one or more wells or thermal channels. Alternatively the gas manifold may be common to all wells and/or all thermal channels. The gas manifold can function to provide a gas to the wells of the array, i.e. as a reagent or to provide an inert atmosphere during synthesis. In addition, the gas manifold could be used to remove gaseous products from the wells during synthesis. Alternatively, the gas manifold may be used to reduce pressure in or draw a vacuum on the wells. Optionally, valves to introduce liquid reagents may be present on the array cover.

The array cover may be designed for a variety of uses. For instance, the array cover may generally provide a seal over the array. Alternatively, the array cover may be patterned to fit over the wells and/or the thermal channels, and provide a seal for individual wells or thermal channels of the array, so as to prevent cross-contamination between wells. The array cover may comprise one or more different features in various combinations, such as a gas manifold and a zinc selenide window in the same array cover to permit the array cover to perform more than one function.

Either of the array or the array cover may comprise a gasket, fabricated by a number of means known in the art. The gaskets may be deposited to be arranged around the individual wells and/or thermal channels of the array. Alternatively, the array cover may be patterned to match the array, and the gasket may be deposited on the array cover. The gasket may comprise a wide variety of materials, which are suitable for this purpose, and are compatible with the reagents and products used in generating the libraries. For instance, the gasket may comprise one or more materials selected from the group consisting of a thin metal film such as gold or carbon, a polymer material including but not limited to fluorinated polymers such as tetrafluoroethylene fluorocarbon polymers and fluorinated ethylene-propylene resins, a rubber material, an elastomer material, and mixtures of these.

Thin films usually have a thickness of about one atom and consist of a metal deposited on a metallic substrate either externally by vapor deposition or internally by diffusion. The base metal is a material such as tungsten (for a cathode) and the film may be any of a number of other metals, such as gold, carbon, thorium, cesium, zirconium, barium, or cerium. In particular, thin metal films such as gold or carbon are suitable for this purpose. Other appropriate materials will be evident to one of ordinary skill in the art.

Elastomers are typically thermosetting high polymers having properties similar to those of vulcanized natural rubber, or uncrosslinked polyolefins that are thermoplastic. Elastomers such as styrene-butadiene copolymer, polychlordprene (neoprene), nitrile rubber, butyl rubber, polysulfide rubber, cis-1,4-polyisoprene, ethylene-propylene terpolymers, silicone rubber, polyurethane rubber and mixtures thereof may also be used. The elastomers may also be further cross-linked with sulfur, peroxides, or similar agents.

Methods of Using the Array and Covered Array

The array may be used in a variety of synthesis, screening, and characterization techniques. In particular, the array is useful for synthesizing combinatorial libraries in the array, followed by screening and/or characterization of individual compounds in the combinatorial library without requiring sample transfer from the array. These combinatorial libraries may include, but are not limited to, a wide variety of compounds such as chemical or biological compounds, polymers, catalysts, superconductors, zeolites, magnetic materials, phosphors, thermoelectric materials, and high and low dielectric materials. This invention allows for the rapid high-throughput synthesis, screening and/or characterization of individual compounds in combinatorial libraries in the same array and in an efficient and economical manner. Moreover, the screening and/or characterization steps may be carried out in a highly parallel, and/or a non-consumptive manner. In preferred embodiments, the array is adapted to the microscale. The invention also relates to process for varying reactants and reaction conditions within different wells of the array, while maintaining high-throughput synthesis, screening and characterization techniques.

In an embodiment of the invention, the starting materials are introduced into the array and under appropriate reaction conditions, the libraries are synthesized. The array has thermal channels, which may be used to control the temperature of the reaction and provide heating or cooling as needed. In this manner, it is possible to run isothermal reactions. Alternatively, the individual thermal channels may provide a range of temperatures in different wells of the array, thereby permitting temperature optimization and thermal characterization studies.

After the synthesis step, the array may be used to screen and/or characterize individual compounds in the combinatorial library, without requiring sample transfer or sample preparation steps. The screening and/or characterization steps may be carried out in a highly parallel manner, where more than one compound is screened at a time. In this manner, data regarding individual compounds or components in the combinatorial library may be collected, and analyzed, i.e. for structure-activity relationships.

Typical screening and characterizing techniques to be used in this invention include: chemical or biological testing, mass spectrometry, reaction calorimetry, parallel reaction calorimetry, parallel differential scanning calorimetry, viscosity measurement, thermogravimetric analysis (TGA), digital autoradiography, thermal imaging, polarimetry, imaging polarimetry, infrared spectroscopy, IR imaging, reflectance spectroscopy, uv-vis spectroscopy, chemisorption, surface area (BET) measurements, uv-vis fluorescence, phosphorescence, chemiluminescence, Raman spectroscopy, near IR spectroscopy, magnetic resonance imaging, NMR spectroscopy, Electron Spin Resonance (ESR) spectroscopy, gas chromatography, high performance liquid chromatography (HPLC), gel permeation chromatography (GPC), temperature rising elution fractionization (TREF), x-ray diffraction, neutron diffraction, refractometry, circular dichroism, turbidimetry, electron spectroscopy, scanning electron microscopy (SEM), transmitting electron microscopy (TEM), scanning tunneling microscopy (STM) and atomic force microscopy (AFM). These techniques may be used alone, or in any combination. The array can also be used for the measurement of chemical and physical properties such as magnetoresistance, conductivity, porosity, solubility, hexane extractables, weatherability, uv-vis stability, scratch resistance, abrasion resistance, wetability, hardness, color, dielectric constant, moisture absorption, drying rate, solvent swelling, gloss, adhesion, heat aging, shear, stain resistance, color fastness, scrub resistance, spreadability, emulsion stability, zeta potential, and contact angle. Any one of these techniques, taken alone or in combination with other techniques may be used in the practice of the invention.

In an exemplary embodiment of the invention, the array can be used for the rapid screening of olefin polymerization catalysts. Several techniques for the characterization of compounds in the array, which are not consumptive, and allow for multiple characterization steps on the same array are possible. Accordingly, the array allows for the rapid screening of various polymer catalysts, the rapid synthesis of combinatorial libraries of polymers, and the characterization of combinatorial polymer libraries. These methods will allow not only for the rapid discovery of new leads in polymer and catalyst chemistry, but also for rapid optimization of leads.

This invention relates to tools for the synthesis, screening, and characterization of combinatorial libraries, as well as methods for the synthesis, screening and characterization of libraries or arrays of compounds, in a highly parallel manner.

The invention relates to an array, which is designed for the synthesis of combinatorial libraries, followed by the screening and characterization of the libraries in the array without requiring sample handling and sample transfer steps. The invention also relates to a covered array, comprising the array and an array cover. The array cover may be further adapted or interchanged, based on the application. For instance, after the synthesis, the array cover may be interchanged with another array cover, which is adapted for screening and/or characterization. Finally, an apparatus comprising the array is also claimed. The apparatus may comprise the array, and at least one of the array cover and a stage. As with the array cover, the stage is adapted for the particular application at hand. For instance, the array can be easily interchanged between different apparatus or stations, as is described in detail below.

Other aspects of the array or array cover with respect to the covered array is generally determined by the use or application of the array, and will be apparent from this discussion, or from this application taken as a whole.

II. Apparatus

The invention also relates to an apparatus comprising an array cover, an array, a stage, and optionally means for attaching the array cover, the array and the stage. The array has been described in detail above, and it is to be understood that the array may have any combination of thermal channels and/or wells having a membrane layer in the bottom of the well. Various other features of the array have also been described in detail, and any of these features, taken alone or in combination may be present.

As mentioned previously, the array cover may also further comprise one or more gas manifolds disposed above the wells. There may be one gas manifold, common to all of the wells. Alternatively, there may be several gas manifolds corresponding to individual wells, or to specific rows or columns. In another embodiment, the array cover may have an array of gas manifolds, disposed over each of the individual wells, so as to avoid contamination. The gas manifolds may be used to introduce a reagent or introduce a gas into the wells of the array, remove gaseous side-products from the wells and/or provide a vacuum to the wells.

FIG. 7 shows an apparatus according to an embodiment of the invention, comprising an array having a plurality of wells (9) and a stage (14), where the stage may further comprises a gas manifold and/or means for regulating temperature or heating. Also shown are a series of holes (13) for attaching the array in an apparatus. The array can be removed after use in a particular technique, and then moved to another apparatus and assembled, i.e. with a new stage or array cover as needed, for a subsequent synthesis, screening, and/or characterization. In the embodiment shown in FIG. 7, there is also a porous intermediate layer between the array and the gas manifold. In this embodiment, gases may enter through the bottom of the wells. This embodiment is particularly useful for applications where the components of the array are heated, or for mass spectrometry, for example.

In general, the apparatus may further comprise means for controlling the temperature of the wells. Such means may be incorporated into any combination of the array cover, the array, or the stage. For instance, the array may further comprise one or more thermal channels, or an array of thermal channels, which are used to regulate the temperature inside the wells. The thermal channels may comprise a coolant, or the thermal channels may be metalized for resistive heating or doped with a dopant. Typical dopants may be selected from the group consisting of boron, phosphorus, and arsenic, and other suitable dopants will be apparent to one of ordinary skill in the art.

In an embodiment of the invention, the stage may comprise a detection means disposed below the wells and in contact with the membrane layer of the wells in the array. For instance, the stage may be a detection stage, and further comprise thermocouples aligned with at least one of the wells. The term thermocouple encompasses devices for measuring or monitoring heat, and includes not only a thermocouple, but also a thermister, a thermometer, and other similar devices. In an embodiment of the invention, the stage may further comprise individual temperature control of at least one well of the array. Temperature control may include heating or cooling, as well as maintaining isothermal conditions.

Depending upon the particular use of the array, the array cover, array, stage, and/or the means for attaching the array cover, array, and stage may be adapted as needed. In the discussion that follows, specific embodiments of the invention are described in detail. This discussion is intended to show examples of how each of the elements of the apparatus will be adapted for various techniques or analysis. Additional objects and advantages of the invention are discussed in the description that follows, and will be obvious from that description, or may be learned by practice of the invention. It is to be understood that both this summary and the following detailed description are exemplary and explanatory only and are not intended to restrict the invention.

A. Thermal Imaging

The invention relates to methods for monitoring the change in heat during a reaction for an array of compounds, and/or individual compounds within the array. The heat generated during a reaction provides useful kinetic data. The wells of the array comprise various reaction mixtures, and a camera is positioned above the array in order to monitor the change in heat and/or temperature of the reaction mixture as the reaction progresses.

The thermal imaging method involves positioning a camera mounted above the wells of the array. The camera comprises a suitable detector capable of responding to the desired radiation. For instance suitable detectors for infrared radiation include MCT or PtSi detectors. In some embodiments, the camera contains an array of detectors so that all samples are examined simultaneously. The camera may be selected from a variety of types of cameras. For example, the camera may be an infrared (IR) camera, ultraviolet (UV) camera, visible (Vis) camera, X-ray camera, electronic gradient camera, or any combination of these. In a preferred embodiment, the camera is one that contains an array of detectors so that all samples are examined simultaneously.

In many cases, the activity of a catalyst is directly proportional to the heat generated by the reaction. By using an infrared camera, it is possible to rapidly screen a two-dimensional array of catalysts, in real time to monitor the activity and lifetime of the catalysts and to estimate the kinetics of the reactions. Thus, the invention relates to the use of thermal imaging for high-throughput screening of catalysts.

Figure 8:
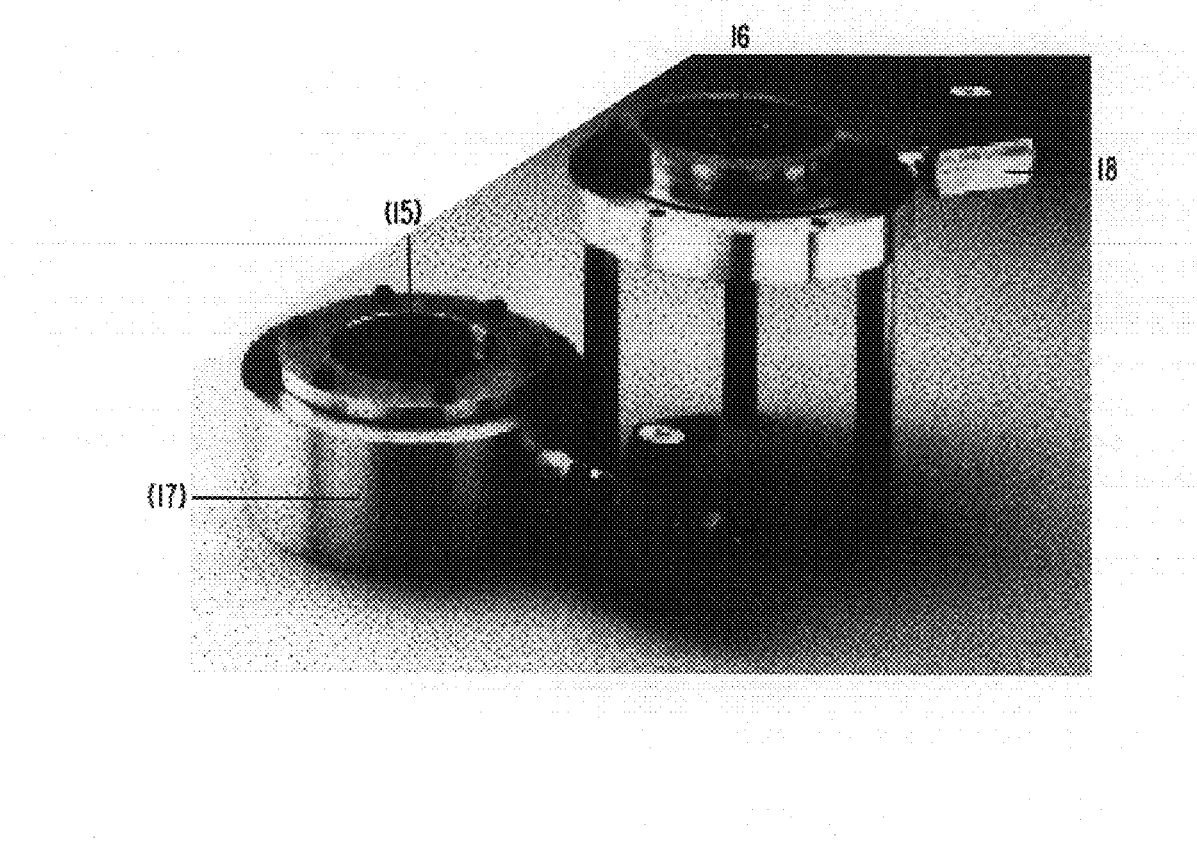
FIG. 8 shows a reaction chamber for thermal imaging of polymerization catalysts. The camera mounted above the chamber is interfaced with a video recorder to monitor heat generation in real time, to produce images as shown in FIG. 9.

When an array cover is used, the array cover will further comprise at least one window, which is transparent to the type of radiation that is being monitored. There may be one window, or there may be an array of windows positioned over individual wells. As shown in FIG. 8, the array cover provides a method of sealing the microarray to prevent gases from escaping and to allow pressurization of the system if desired.

The array cover is shown in FIG. 8. The array cover comprises a IR transparent window (15). The material for the window should be selected such that it is transparent to the source of radiation. In one embodiment, zinc selenide, which is transparent to infrared radiation in the range of 4000 $cm^{-1}$ to 700 $cm^{-1}$ and is able to withstand conditions of 300° C. and 1000 psig, was used. The pressure rating is determined by the relative thickness of the material compared to the area of the window. The frequency response and physical properties of windows can be obtained from optical companies such as Janos Technology, Townshend, Vt.

In one embodiment, an infrared (IR) camera is used, and the apparatus further comprises a coiled tube from which cooling liquid can be added to remove heat from the IR window as necessary. Cartridge heaters will heat the samples to appropriate temperatures. A channel drilled from the side to the center of the baseplate will allow the introduction (or exit) of gases. To ensure a uniform distribution of the gases, channels are machined in a radial direction from the center of the hole. In this embodiment, the array consisted of a glass plate comprising 96 wells with a volume of approximately 8 microliters spaced 4.5 mm from center to center to provide for thermal and chemical isolation as well as dispensing of reagents by commercially available micropipetters.

FIG. 8 shows a reaction chamber for thermal imaging of polymerization catalysts. The catalysts are introduced into each microwell and the sample array is placed directly on the baseplate and heated to the desired temperature by controlling the cartridge heaters. The reactant or reactants for the polymerization, such as ethylene are introduced through the channel in the baseplate to allow a uniform distribution of the gases. The camera mounted above the chamber is interfaced with a video recorder to monitor heat generation in real time, to produce images as shown in FIG. 9.

Figure 9:
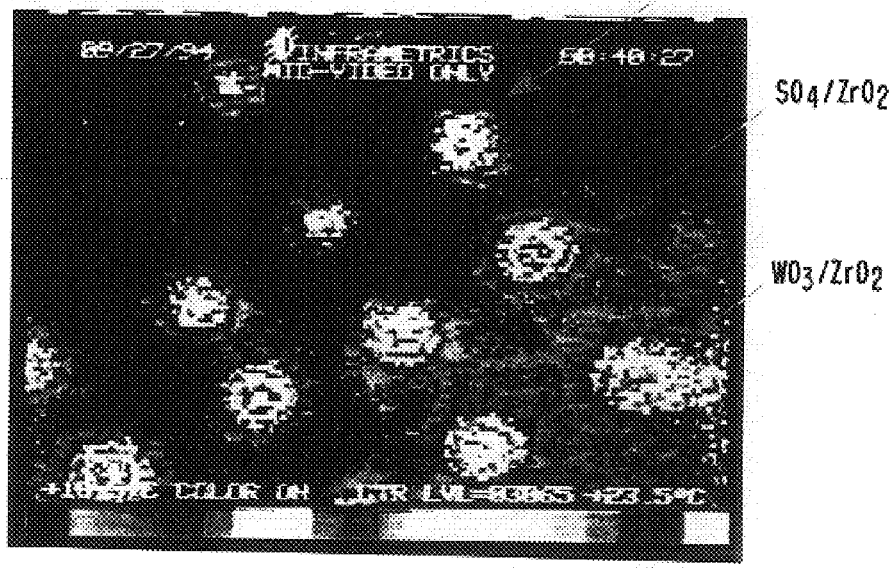
FIG. 9 shows an image of various solid acid and zeolite catalysts as monitored in the array. The thermal image indicates that higher levels of heat generated for those wells correspond to (1) Zeolon™ which is commercially available from Norton, Worchester, Mass., (2) $SO_4/ZrO_2$, and (3) $WO_3/ZrO_2$.

In FIG. 9 various solid acid and zeolite catalysts are in the array, and the thermal image indicates that higher levels of heat generated for those wells correspond to (1) Zeolon™ which is commercially available from Norton, Worchester, Mass., (2) $SO_4/ZrO_2$, and (3) $WO_3/ZrO_2$. In this example a Thermacam 290, commercially available from Inframetrics, located in North Billerica, Mass. that has an accuracy of better than 0.1° C., was used. The camera is estimated to be sensitive to 0.1° C. The minimum material required for adequate detection varies widely with the concentration of active sites and exothermicity of the type of reaction screened. For the thermal image in FIG. 9, milligram quantities of solid acid catalysts were used. For ethylene polymerization catalysts, nanogram quantities are often sufficient.

In a preferred embodiment, the thermal imaging techniques are used to filter out catalysts with little or no activity. Promising catalysts are then be screened under more rigorously controlled conditions in the parallel reaction calorimeter discussed below.

B. Parallel Reaction Calorimeter

The thermal imaging methods described above may be used, even without a means for temperature control and for running the reactions under isothermal conditions. However, some reactions, such as catalytic polymerizations, for example, are particularly sensitive to temperature and catalyst screening is most effectively run under isothermal conditions because small deviations in temperature can have very large effects on activity or reaction products. Thus, the invention relates to a parallel, high-throughput process for the synthesis, screening, and characterization of combinatorial libraries under isothermal conditions.

In an embodiment of the invention, a parallel reaction calorimeter is used in a process for monitoring the array in a highly parallel fashion. In this embodiment, at least one well contains at least one compound, and the stage comprises means for individually monitoring heat emitted from at least one well. The characterizing step comprises the steps of maintaining isothermal conditions in at least one well; and monitoring the heat required to maintain isothermal conditions in the at least one well. For polymerization reactions, integration of the activity data allows the determination of the mass of the resulting polymers, which can then be used to determine important figures of merit in subsequent analyses.

In an embodiment of the invention, the array cover comprises one or more gas manifolds, which allows for several different sets of monomer gas feeds and/or pressures to be used throughout the array. The array cover is fabricated from a reusable, stainless steel gas manifold. The feed gas, provided by a simple olefin feed, is divided into a series of manifolds. If desired, different feed gases can be used, each connected to a different manifold so that several olefins or olefin combinations can be fed into the wells of the array. The feed pressure(s) are regulated by conventional pressure gauges from the source. If necessary, microcheck valves can be positioned at the end of each manifold exit.

The invention further comprises means for maintaining isothermal reaction conditions in at least one well. In an embodiment of the invention, the means for maintaining isothermal reaction conditions may comprise thermal channels. The array consists of a disposable array of wells traversed by cooling channels, preferably microfabricated on a silicon wafer. A gold foil gasket is microdeposited around each well to prevent cross-contamination. The bottom of each well comprises a very thin membrane to allow for vibration and rapid heat transfer between the sample and the stage, which comprises heater/temperature sensors.

The stage comprises an array of heater/temperature sensors, which provide for individual temperature control of each well. Microheating and temperature sensing are modified to incorporate an integrated thermal heating/cooling system for this application. See S. Oh, W. Chu, S. Cahill, *Proceedings of the* 1992 *Spring Meeting of the Materials Research Society*, San Francisco, which is hereby incorporated by reference. Preferably, the microheater and temperature sensors are made by using a thin film of platinum, and the temperature ratings of the heaters are in excess of 500° C.

An array of microcalorimeters will analyze catalyst activity and the thermal behavior of the resulting products. The reaction calorimeter provides a means to conduct isothermal reactions to produce more refined data than that from thermal imaging. Cooling channels, combined with an array of microheater/temperature sensors, will control the temperature of the reaction wells; the heat input required to maintain the reaction is monitored and associated with the exothermicity (and thus, activity) of the polymerization.

To maximize the sensitivity of this device, engineering calculations and feasibility experiments were conducted to ensure that heat is not dissipated into the surrounding environment and to provide efficient response times during the polymerization reaction. The preferred well size is 0.25 to 8 μL, which allows the relatively facile fabrication of reaction well arrays on silicon wafers and gives low ongoing cost. However, much larger well sizes can be fabricated by using a glass-silicon hybrid structure, in which the walls of the reactor are glass and the bottom of the well is a thin silicon membrane.

A cross section of an embodiment of the array used for reaction calorimeter is shown in FIG. 10. As shown, the array comprises at least one reaction well (9), which contains a reaction mixture (22). There are thermal channels (8) surrounding the well (9), which are shown as cooling channels in this embodiment, and a gasket/gold seal (11) surrounding the edge of the well. In this embodiment, the wells comprise a thin silicon membrane forming the bottom of the well. The stage (20) further comprises a heater/temperature sensor (21). The array cover (19) comprises a reusable stainless steel gas manifold and, optionally, valves to inject solutions (not shown).

In one embodiment, the reaction calorimeter is composed of three sections, as shown in FIG. 11, which may be mechanically clamped together. The array cover (19) comprises an array of gas manifolds (23), which are positioned over individual wells. In this embodiment, the array comprises cooling channels (8), and gasket/gold seal (11) disposed around the edges of each well. The wells further comprise a membrane layer forming the bottom of the well, and in direct contact with the stage (20). The stage comprises an array of heaters/temperature sensors (24), corresponding to the wells.

In an embodiment of the invention, the parallel reaction calorimeter provides activity data for reactions, and in particular, for catalysts held under isothermal conditions. The amount of heat input required to maintain each well at the desired temperature is inversely proportional to the activity of the catalyst. For example, polymerization reactions are exothermic; the most active catalysts will require the least heat input to maintain the desired temperature. The heat input/time profile provides reaction kinetics and catalyst stability data. The temperature control results in much more reliable kinetic data than that provided by thermal imaging. The parallel reaction calorimeter design provides for independent variation of catalyst, cocatalyst, solvent, monomer, and temperature within the array for optimization of reaction conditions. For instance, the parallel reaction calorimeter of the invention may involve the use of an array which has wells, having a volume of about 1 μL to about 8 μL, where the array may contain about 100 wells, and be fabricated from silicon.

C. Parallel Differential Scanning Calorimeter

The invention also relates to a parallel differential scanning calorimeter. For the parallel differential scanning calorimeter, the protocol is the same as for the differential scanning calorimeter described above, with the following differences:

1. Solvents, and liquid or gas reactants from previous steps are removed by evaporation prior to analysis;
2. The stage comprises a reference material, and a corresponding electrode;
3. The array cover is not necessary; and
4. If the parallel differential scanning calorimeter is used following reaction calorimetry, the sample mass may be determined from integration of activity data. However, it is to be understood that the differential scanning calorimeter could also be used independently.

Thus, the invention relates to methods for determining the melting point of compounds in the array. In particular, the invention relates to a process where a combinatorial library is generated, and any solvents are removed by evaporation. Next, the components of the library, and a reference material are heated at the same constant rate. The reference material is selected from a material that does not exhibit thermal transitions under the conditions used for the measurement, i.e. constant input of heat. In a preferred embodiment, the reference material is located in the stage. The differential scanning calorimeter technique involves heating the sample and a reference material at a constant rate and measuring the difference in heat fluxes required to keep the temperature of the sample equal to that of the reference. Variation from the baseline indicates melting (endothermic) or crystallization (exothermic) within the sample. The peak areas are directly proportional to the enthalpy change of the phase transitions. The sample size for parallel reaction calorimeter is typically about 1 mg, or in the ranges of about 1 ng to about 100 mg, about 1 microgram to about 10 mg, or about 50 microgram to about 1 mg.

Monitoring the heat input to each sample indicates the temperature ranges of endothermic (melting point) or exothermic phase (crystallization) changes in the polymers. By inputting the relative mass of each sample (from activity data), the relative heats of fusion for each process may also be determined. This data provides a measure of the crystallinity of the sample to indicate the microstructural attributes, such as tacticity and comonomer content, of each component of the array.

The parallel differential scanning calorimeter has a thermocouple monitoring a reference material, which is connected in series to the samples. The stage comprises an array of heaters/temperature sensors corresponding to the wells of the array. In addition, the stage comprises a reference material and heaters/temperature sensors connected in series to those of the array. The heating stage comprises at least one thermocouple attached to at least one well and at least one thermocouple measuring the reference temperature of a reference compound. The thermocouple measuring the reference temperature of the reference compound is attached in series to the at least one thermocouple attached to the at least one well.

In a preferred embodiment, the invention relates to a method for measuring the crystallinity of combinatorial libraries of polymers. Crystallinity is an important determinant of the utility and application of a polymer. In an embodiment of the invention, the parallel differential scanning calorimeter is used for the high-throughput analysis of polymer crystallinities. This technique is integrated with the parallel reaction calorimeter to preclude the need to weigh and transfer the polymers.

D. Viscosity/Stiffness/Mass Sensor/Thermogravimetric Analysis

The invention relates to methods for determining the viscosity, stiffness, mass, and thermogravimetric properties of a combinatorial library, or of individual compounds within the library. In an embodiment of the invention, the invention relates to a non-consumptive technique for measuring the viscosity, stiffness, and heat deflection temperature of components within the array. The invention thus relates to a viscosity/stiffness sensor that uses the principle of electrostatic forces to cause vibration of the thin membranes fabricated into the array. The viscosity sensor is based on an electrostatic interaction to induce vibrations of the silicon membrane that forms the bottom of the reaction well.

The invention also relates to thermogravimetric analysis techniques. These techniques are used to measure the change in weight of a sample with rising temperature. The change in temperature may be related to the evolution of a gas, for example. The protocol is the same as that described for the viscosity sensor, where the change in mass of the sample affects the vibration of the membrane.

According to a method of the invention, the amplitude of vibration of the membrane will vary with sample mass and viscosity (or stiffness). It is possible to subtract the effect of polymer mass through correlation with polymer activity data. This viscosity/stiffness sensor measures the viscosity, stiffness, and heat deflection temperature of components in the array. In another embodiment, the viscosity/stiffness/mass sensor functions as a thermogravimetric analyzer, determining the change of sample mass with rising temperature.

For polymer applications, the viscosity data for polymers obtained from the viscosity/stiffness/mass sensor is related to the melt flow rate of the polymer. If measurement is following reaction calorimetry, sample mass may be determined from integration of activity data. It is to be understood that the viscosity/stiffness/mass sensor may also be used independently.

In this embodiment, the invention relates to an apparatus comprising an array and a stage, a means for applying a voltage across the membrane of the well and, optionally, an array cover. A cross section of an embodiment of the viscosity/stiffness sensor is shown in FIG. 12. In this embodiment, the stage (25) is a proximity sensor stage, comprising a fiber optic detector, which is capable of optical detection (29). An indium tin oxide (ITO) electrode (27) is used to apply alternating electrostatic potential to induce vibration of the membrane(s). As shown in FIG. 12, the sample (28) is contained in a well (9), and the bottom of the well comprises a thin silicon membrane (10) comprising a thin, reflective metal coating (12).

The bottom of each well in the viscosity/stiffness sensor is covered with a reflective metal coating, allowing for the electrostatic vibration of the well membranes. According to this process, the membrane is subjected to alternating electrostatic potential to cause vibrations, which can then be measured by optical detection. The bottom of the microwells have a thin metal coating to enable electrostatic vibration of the membrane and, for the embodiment involving optical detection, to reflect incident light. In a preferred embodiment, the array will comprise thermal channels and the thermal channels are used to heat the samples. The samples may also be heated by using an oven.

In another embodiment of the invention, an array of proximity sensors, measuring capacitive, electric, or magnetic fluctuations, detect the amplitudes of vibrations of the membranes. The primary types of commercially available proximity sensors measure inductive, capacitive, and magnetic changes caused by the vibrating membrane. Such proximity sensors are commercially available from Keyence Corporation of America, Woodcliff lake, N.J. A variety of proximity sensors may be used, such as but not limited to inductive gauging sensors, inductive displacement sensors, laser displacement sensors. A variety of linear displacement measuring and gauging with inductive sensors are also commercially available, i.e. from Micro-Epsilon, Raleigh, N.C. A variety of capacitive sensors and eddy current proximity switch sensors are commercially available from Gordon Products, Inc., Brookfield, Conn.

In one embodiment of the invention, an optical fiber array is used to transmit and receive the light reflected from the membrane. In this case, the rigid electrode must be constructed from an optically transparent material, such as indium tin oxide (ITO). The amplitude and frequency of the vibration is directly related to the mass and viscosity of the component contained in the array.

In an embodiment of this invention, the above method is applied to analyze polymers. According to a method of this invention, the amplitude of vibration of the membrane is affected by the polymer mass and mechanical properties. In one embodiment of the invention, the relative mass of a polymer is calculated from activity measured by reaction calorimetry. The effect of polymer mass on the data is subtracted by calculating the yield from activity data of the polymer sample.

The resulting viscosity data is related to the melt flow index of the polymer, which is an important indication of polymer processability. By varying the temperature from ambient to above the melting point of the polymer, it will also be able to detect the heat deflection temperature or softening point of the polymers. The amplitude of the vibration at temperatures below the softening point provides a measure of the stiffness the polymer. The samples are heated using the thermal channels of the array. In another embodiment of the invention, the entire viscosity/stiffness sensor is contained within an oven to enable measurements at elevated temperatures.

By conducting the experiment under different conditions (temperature and applied electrostatic potential), it is possible to acquire data for the three polymer properties: stiffness, heat deflection temperature, and viscosity. At a constant temperature, the measurement of vibrational amplitude with respect to alternating electrostatic potential provides a measure of the stiffness of the polymers. Alternatively, a constant alternating potential is maintained while increasing the temperature of the array. The temperature at which the membrane begins to vibrate indicates the heat deflection temperature of the polymer. Finally, at temperatures about the melting point of the polymer, the amplitude of vibration indicates the viscosity of the polymer melt; which can be related to melt flow rate data of bulk polymers. Because the stiffness and temperature deflection measurements are often on sample preparation, these techniques are typically used to make relative comparisons polymers of similar composition that have undergone an identical annealing process.

E. Digital Autoradiography

One embodiment of the invention relates to an apparatus comprising an array, an array cover, and a stage. The apparatus further comprises means, positioned over the array, for measuring the radioactivity of at least one well. In an embodiment of the invention, the means for measuring radioactivity is an autoradiograph.

The invention relates to a process of characterizing compounds, comprising the steps of providing an array comprising compounds that have incorporated at least one radio-labeled compound. In a preferred embodiment, the compounds may be synthesized by adding at least one compound, such as a catalyst to each well, and providing at least one radio-labeled reagent in at least one well. The at least one radio-labeled reagent reacts in at least one well to form a radio-labeled compound. Optionally, any materials other than the compound of interest, are removed, and the array is transferred to an autoradiograph. The radioactivity of at least one well is then measured. In a preferred embodiment, the radioactivity of more than one well is measured at a time, in a parallel manner.

Typical autoradiographs which are used in this invention include those commercially available from sources such as EG&G Berthold, Gaithersburg, Maryland. Typical models used include, but are not limited to the LB 287 Digital autoradiograph, and LB 285 and LB 284 Linear Analyzers.

The invention also relates to a process that further comprises the step of determining the comonomer content of a component formed in at least one well. In an embodiment of the invention, the process further comprises the step of determining the surface area or porosity of an inorganic compound in at least one well. In another embodiment of the invention, the process further comprises the step of determining the extent of tritium incorporation for the hydrogenation of an unsaturated substrate. The invention is adaptable to a wide range of radiolabeled reagents. For instance, the radiolabeled reagent may contain at least one of the following nuclei: $^3H$, $^{14}C$, $^{32}P$, $^{35}S$, $^{36}Cl$, $^{85}Kr$, Rn, as well as others that are known in the art.

In a preferred embodiment, the invention relates to a process for the determination of comonomer content in a polymer. Comonomer content of a polymer is conventionally measured through time intensive techniques such as NMR spectroscopy. This invention provides a method to measure the comonomer content of a large array of copolymers simultaneously, which will reduce analysis time by two orders of magnitude compared to conventional techniques. The technique of the invention provides a means for the rapid discovery of new catalysts for copolymers such as linear low density polyethylene, of which several million tons are produced every year. In this embodiment, the radiolabeled reagent may be introduced through at least one gas manifold in the array cover. The array may have an array of gas manifolds, which allows for several different reagents to be introduced into each well of the array.

Radiolabeled comonomers are prepared from commercially available isotopically enriched materials as shown in the following scheme:

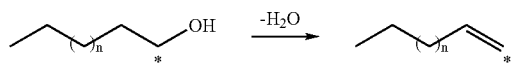

The radiolabeled carbon in this scheme is indicated by the asterisk (*). Monomers and labeled comonomers are then fed into a 2-dimensional array of catalysts. If the autoradiography measurement are taken following reaction calorimetry, sample mass may be determined from integration of activity data. It is to be understood that the digital autoradiograph may also be used independently.

Each catalyst is likely to incorporate different proportions of monomer and comonomer into the resulting polymer. After the reaction is stopped and the volatile solvent, monomer, and comonomer are removed, the array is transferred to a modified commercial digital autoradiograph. The resulting digital image indicates which polymers contain the most radiolabeled comonomer.

In one embodiment of the invention, the relative mass of the polymer is calculated from activity measured by reaction calorimetry. The relative comonomer reactivity ratios can then be determined for each catalyst in the array. It is to be understood that the autoradiography screen may also be used independently.

F. Mass Spectrometry

The invention also relates to mass spectrometry techniques adapted for combinatorial chemistry. In one embodiment, the invention relates to mass spectrometry designed for the analysis of product gases, and is typically a reaction time measurement, for example. In a second embodiment of the invention, mass spectrometry is used for the analysis of solids (a product time analytical technique).

An embodiment of the invention is shown in FIG. 13. In this embodiment, the mass spectrometry apparatus comprises the array cover (30), the array (32), the stage (14), a mass spectrometer, and means for heating the samples in one or more wells. The array cover (30) comprises a gas manifold, which is in flow communication with the mass spectrometer. As shown in FIG. 13, the stage (14) comprises a porous stainless steel 316L membrane (34), a backing plate (35), a deflector plate (36), a gas inlet chamber (37), and a gas inlet (38). The array (32) is in contact with the stage (14), and the stage provides a heat source to the wells of the array. The array cover comprises tubes (31) leading to sampling valves, which allow the products from, selected microwells to be examined by the mass spectrometer.

FIG. 14 and FIG. 15 show further views of an embodiment of the invention. Also FIG. 7 shows an embodiment of the invention where the array (32) and stage (14) are assembled, without the array cover.

The mass spectrometer can detect the molecular mass of each component eluting from the array, as well as the masses produced by a molecule when it fragments upon being ionized at the mass spectrometer ion source. In cases where masses of the various species overlaps the fragmentation pattern of the molecules can be used to help identify the identify the components. A discussion of the use of mass spectroscopy for identification of organic compounds can be seen in Silverstein, et al., *Spectromethic Identification of Organic Compounds, Fifth Edition*, John Wiley and Sons, Inc., New York, N.Y. (1991). The information from these masses is used to identify the product profile as well as to provide both activity and selectivity measurements for the catalyst or process occurring in each microwell. The apparatus further comprises means for attaching the array cover, the array and the stage.

In an embodiment of the invention, the apparatus is adapted for determining the absolute molecular weight and/or molecular composition of solids within the array. The invention relates to the array, a mass spectrometer equipped with a robot to allow for manipulation of an array of samples in the vacuum chamber, and optionally, a means to dispense matrix elements into the array.

In one embodiment of the invention, the molecular weight (MW) and molecular weight distribution (MWD) of polymer samples, which can have a large effect on physical properties, are determined. Mass spectrometry is used for the high-throughput screening of the MW and MWD of polymers. This technique has the advantages of rapid analysis, microscopic sample size (µg), and the determination of absolute MW (rather than comparison with standards). In this embodiment an array containing polymer samples is prepared and, optionally, charged with a solution of matrix. The matrix and solution are typically used for MALDI, but are not required for SALI. The solvent, is allowed to evaporate and the array is placed into a vacuum chamber equipped with a robot for manipulation of the array. The samples are then characterized using a mass spectrometry technique such as MALDI or SALI.

The mass spectrometer may be used in a variety of mass spectrometry methods. For example, matrix-assisted laser desorption/ionization (MALDI) of large organic molecules was introduced in 1985 by Hillekamp and coworkers for amino acids. See M. Karas, D. Bachmann, F. Hillenkamp, Anal. Chem., 57:293 (1985), which is entirely incorporated by reference. Since then, the field has rapidly developed and has been extended to many classes of molecules including synthetic polyolefins, such as polystyrene and poly (methylmethacrylate) having molecular weights between 1000–100,000 and narrow MWD. See H. Chen, B. Guo, Anal. Chem., 69:4399 (1997), A. T. Jackson et al., J. Am. Soc. Mass Spectrom., 9:269(1998), and A. T. Jackson et al., J. Am. Soc. Mass Spectrom., 9:269 (1998), which are entirely incorporated by reference. MALDI analysis involves dissolution of the analyte with an excess of a matrix, which is typically an aromatic alcohol or acid that absorbs at the wavelength of the laser. The sample molecules are then desorbed/ionized by a pulsed laser beam and analyzed in the mass spectrometer. The matrix serves to transfer charge to the polymer molecules, minimizing sample degradation.

Surface Analysis by Laser Ionization (SALI) is a mass spectrometric technique used for the mass analysis of solid samples, as described in U.S. Pat. No. 4,733,073 and S. P. Mouncey, L. Moro, C. H. Becker, *Appl. Surf. Science* 52:39 (1991), which are both hereby incorporated in its entirety. In the SALI method, neutral atoms and molecules are desorbed from the surface of a sample, converted to positive ions by laser ionization, and detected using time-of-flight mass spectrometry (TOF-MS). Desorption may be achieved using a variety of methods, including bombardment with energetic neutral atoms, electrons, or laser radiation. Laser post-ionization can be performed either using non-resonant multiphoton ionization, or by single photon ionization (SPI). The latter method has been developed at SRI as a tool for surface analysis and organic compound characterization (C. H. Becker, Fresenius J. Anal. Chem., (1991) 341, 3, which is hereby incorporated in its entirety). In the SPI approach, 118-nm photons (energy=10.5 eV, 9th harmonic of a Nd:YAG) are used for photoionization. TOF-MS measures the transit time of ions with a known, fixed energy over a fixed distance. This directly yields their mass-to-charge ratio, which for singly charged ions, is their atomic or molecular mass.

The SPI-SALI approach to photoionization mass spectrometry has been successfully applied to the study of a large variety of molecules on surfaces. Among these examples are amino acids and peptides (C. H. Becker, L. E. Jusinski, L. Moro, Int. J. Mass Spec. Ion Proc. (1990), 95, R1; C. R. Ayre, L. Moro, C. H. Becker, Anal. Chem. (1994), 66, 1610, which is hereby incorporated in its entirety), and polymers (J. B. Pallix, U. Schuhle, C. H. Becker, D. L. Huestis, Anal. Chem. (1989),61, 805, which is hereby incorporated in its entirety). In the current literature, applications of TOF-MS using 118-nm SPI are described where the visible UV light was used to ionize and detect small polymers (M. S. deVries et al., J. Photochemistry and Photobiology A Chemistry (1997) 106, 31, which is hereby incorporated in its entirety) in gaseous form.

Several advantages of SPI with 118-nm photons have been pointed out in the literature regarding the characterization of compounds on surfaces. For instance, non-specific fragmentation of molecular species is avoided or strongly reduced because molecules with an ionization potential (IP) below 10.5 eV, which represent a large fraction of the more common compounds, are ionized by adsorption of a single photon. This results in only a minimal amount of excess energy remaining in the ionized molecule, thus decreasing the probability of non-specific fragmentation. Nevertheless, breaking of weaker or specific bonds may occur, producing characteristic ionized fragments that allow species identification and molecular structure investigation.

Surface analysis of laser ionization (SALI) techniques use a combination of (1) a desorption beam, either a laser or an ion beam, or some other form of localized vaporization, (2) an ionization laser to produce positive ions from the thermally vaporized or ablated neutral molecules, and (3) a time-of-flight mass spectrometer to determine the mass-to-charge ratio of the laser-produced ion. According to the invention, the SALI techniques can be extended to simultaneously perform multiple analysis in parallel using a two-dimensional detector. One embodiment of the invention relates to combinatorial methods to chemically analyze new materials produced as a result of combinatorial synthesis wherein large array reaction wells are filled with varying mixtures of reactants. This invention will permit the simultaneous characterization of the products formed in one row of wells. A second embodiment of the invention will be used to perform simultaneous analysis of gas phase (vapor) products formed in a row of wells as a result of catalytic reactions with each well, for example. An embodiment of the invention relating to a combinatorial process for performing mass spectrometric analysis of multiple solid or vapor samples in parallel is illustrated in FIG. 17 through FIG. 22.

As shown in FIG. 17, varying amounts of selected reactants are placed in each well according to standard combinatorial practice. The array (or well plate) (52) is then placed in contact with the cover, here an aperture plate (53), which may form the external vacuum wall of the time-of-flight mass spectrometer. The reaction wells may be maintained at an elevated temperature to promote chemical reactions. Analysis of the gas phase reaction products occurs when the sliding vacuum valve (54) is moved to expose the row of inlet apertures and the reaction array (52) is translated so as to align all wells in a single row with the corresponding apertures (55). The gas phase contents of each well are admitted into the vacuum system in the form of spatially localized molecular beams that are subsequently ionized by a pulsed laser propagating just above and along the row of apertures.

As shown in FIG. 18a (the reactant gas dosing phase), wells (56) containing varying mixtures of selected catalyst materials are prepared and dosed with selected reagent gas at high pressure. The aperture plate (53) and array (52) are separated and the sliding vacuum valve (54) is closed to preserve the high vacuum of the mass spectrometer. As shown in FIG. 18b (the reaction phase), the array (52) is moved into close contact with the aperture plate (53) to prevent communication between wells. The sliding vacuum valve (54) is closed to preserve the high vacuum of the mass spectrometer. The array (52) can be heated as necessary to promote reactions. The analysis phase is shown in FIG. 18c; the array (52) is translated with respect to the aperture plate (53) to align one row of wells with the apertures. The sliding vacuum valve (54) is opened to admit any gas phase products in the row of wells into the high vacuum of the mass spectrometer. A pulsed laser is directed along the row of neutral molecular beams that form as a result of the expansion of the high pressure vapors contained in each well. The resulting spatially localized ion beams formed by laser ionization are analyzed by both well position and mass-to-charge ratio as shown in FIG. 19.

As shown in FIG. 19, the parallel ion beams formed by laser ionization of the spatially localized molecular beams are extracted and maintained parallel using appropriate electrostatic elements, then accelerated to a uniform energy. In a field free region at a distance from the extraction region, the parallel ion beams pass through a pair of electrostatic deflectors upon which is impressed a time varying voltage whose timing and waveform are chosen to deflect the ions orthogonal-to their flight path such that the lateral deflection is a linear function of the mass-to-charge ratio of the ions. Upon exiting the deflection region, the ions again traverse a field free region where they subsequently impinge upon a 2-dimensional, charge integrating detector, such as a charge-couple device (CCD). The charge accumulated at each x position (horizontal time axis) for a given y position (vertical well position) corresponds to the ion intensity originally present in a given reaction well.

Figure 20B:
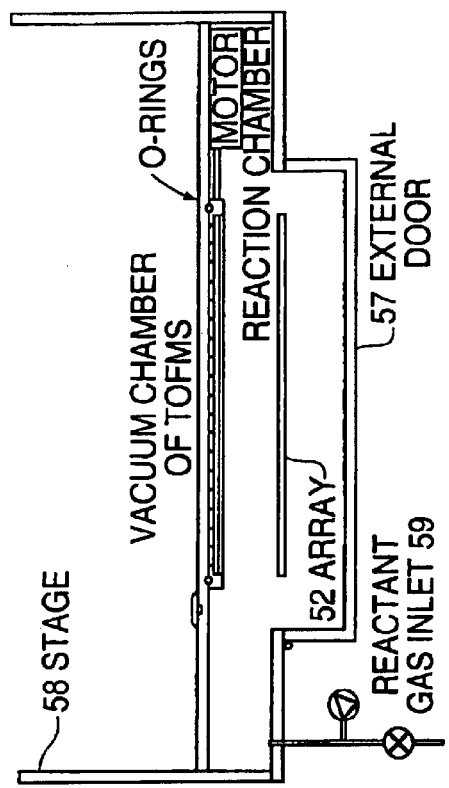
Figure 20D:
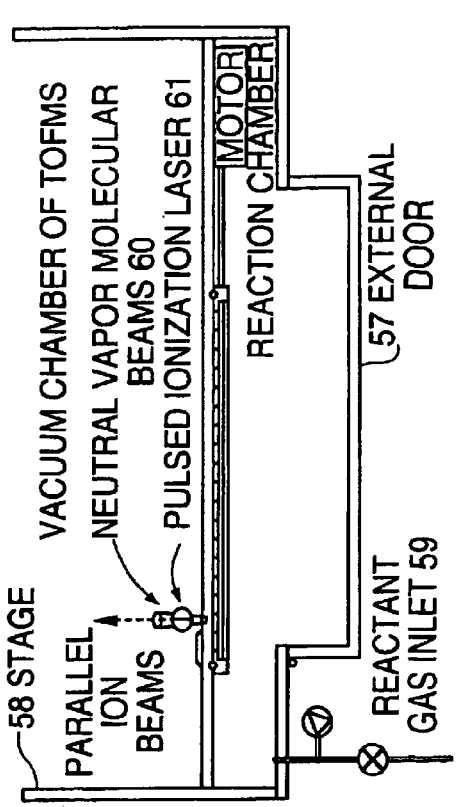
Figure 20A:
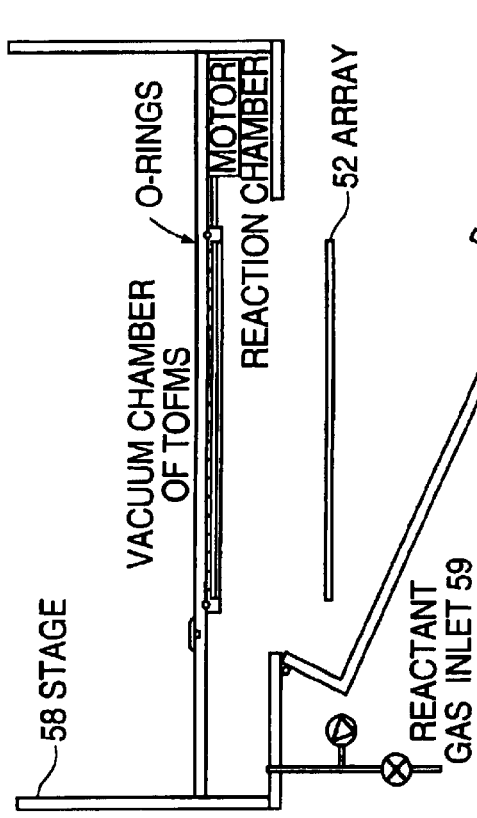
Figure 20C:
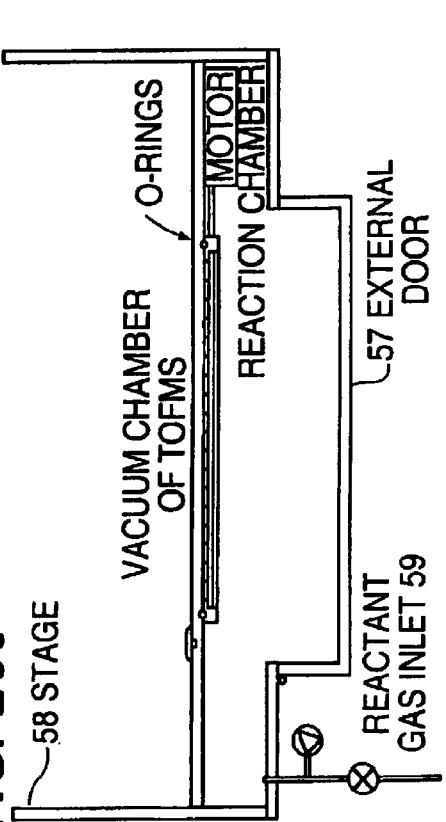

As shown in FIG. 20a, a stage (58) having the external door (57) to reaction chamber and a reactant gas inlet (59) is opened to load a array (52). Combinatorial materials can be pre-deposited into wells before loading, or deposited after loading. In FIG. 20b, the external door (57) to reaction chamber is closed. Reactant gas is admitted into reaction chamber at desired pressure. In FIG. 20c, the array (52) is clamped to a translating plate containing an array of apertures that are larger in diameter than the row of apertures between the reaction chamber and the vacuum chamber. The array of large apertures align with the array of reaction wells. The reaction wells can be heated to promote catalytic reactions. In FIG. 20d, the sliding vacuum valve is opened and the large aperture plate/array is translated by a motor system to align one row of reaction wells with the row of apertures in the vacuum chamber wall. A pulsed ionization laser beam (61) propagates just above and along the row of spatially localized neutral vapor molecular beams (60) formed at each aperture thereby producing ions characteristics of the reaction products from each well.

An alternative configuration using volcano field ionization sources is shown in FIG. 21. In this configuration, the function of the sample entrance apertures is achieved through the use of multiple microfabricated volcano field ionization sources aligned in a row. Sample vapors from a row of reaction wells is introduced into the funnel side of the volcano sources by moving the array relative to the fixed cover plate (62) containing the volcanoes until a row of wells is aligned with the row of volcanoes. Because of structural considerations, the volcanoes cannot be sealed on the vacuum side to maintain the low source pressure when no sample is present. Vacuum sealing would either be accomplished from the funnel side of the volcanoes, or the reaction array would be introduced into the vacuum region prior to analysis. This configuration is most suitable for the analysis of organic/polymer materials with molecular weights in excess of 58 Daltons. Sample vaporization can be achieved by thermal means on a row-by-row basis using heating elements such as thermal channels integral to the array, or heating elements in the stage, or heating elements incorporated into a separate plate that contacts the array from the non-well side.

Parallel TOFMS for Bulk/Surface composition analysis is shown in FIG. 22. For the chemical characterization of solid materials such as catalysts, the vaporization/ablation process is separated from the ioninzation process as the SALI approach. A pulsed laser, for example, can be directed through a series of properly oriented reflectors onto multiple vaporization sites (reaction wells) simultaneously. The resultant neutral vapor plumes will be spatially localized for a time sufficiently long that a second pulsed laser propagating just above and along the row of wells will simultaneously produce ions of characteristic mass-to-charge ratios from the neutral vapors in each plume. The resultant spatially localized, parallel ion beams are then extracted, separated, detected, and analyzed using the methods described in FIG. 19. During the analysis operation, the row of wells being characterized must be maintained under the vacuum conditions typical of the source region of a laser ionization mass spectrometer.

III. Combinatorial Chemistry Process

The invention also relates to a combinatorial chemistry process, used for the synthesis of compounds in combinatorial libraries in a highly parallel manner. According to this process, combinatorial chemistry is used to create large collection of molecules, which are known as libraries, and which can be screened together. Combinatorial libraries may comprise mixtures of compounds, or may comprise an array of individual compounds in each well of the array.

In cases where mixtures of compounds are synthesized, screened and/or characterized, there is often also a method of identifying compounds of interest. These methods may be either spatial, (such as through spatially addressable synthesis or chemical encoding), or systematic, (such as through a series of deconvolutions). Spatially addressable synthesis refers to the generation of an array of compounds where each reaction well comprises an individual reaction product or compound. Chemical encoding may take the form of a number of inert chemical tags to identify each compound. Iterative deconvolution involves the identification of the most active mixture, followed by fixing some specific part of the molecule and making a smaller library; this process is repeated until a single compound is identified. Other deconvolution, positional scanning, and encoding methods are known in the art. See Wilson, S. R. and Czarnik, A. W., Eds., Combinatorial Chemistry, John Wiley & Sons, New York, 1997, which is hereby incorporated in its entirety.

The invention relates to a process comprising the steps of providing an array, introducing at least one reagent to at least one well of the array, and reacting the reagent in at least one well to form at least one compound. The array has been described in detail above. In addition, the reaction may be run in an apparatus optionally comprising an array cover, an array, a reaction stage; and means for attaching the array cover, the array, and the reaction stage. Optionally, the array cover may comprise at least one gas manifold. These features will depend, to a large extent, on the particular application used, and will be apparent to one of ordinary skill.

For instance, some reactions will require an inert atmosphere, or have gaseous reagents. In these cases, the array cover may further comprise at least one gas manifold. For some reactions or processes, the reactions will need to be heated. In such instances, the stage should further comprise means for heating, such as individual thermocouples or a heating block. After the reagents are introduced into the array, the reaction may proceed through solution phase chemistry, photochemistry, polymerization, by heating, by irradiating, and other methods as are known in the art. The combinatorial chemistry process may involve any type of chemical reaction.

The chemical reactions generally involve a chemical change that occurs through a number of ways, such as, but not limited to: combination, replacement, decomposition, oxidation, reduction, ionization, combustion, polymerization, hydrolysis, hydrogenation, hydrosilylation, hydrocyanation, hydroformylation, carbonylation, isomerization, metathesis, cross coupling, hydration, dimerization, condensation, enolization, saponification, rearrangement, phase changes, changes in physical strucuture, or modifications of these. The chemical reaction may also include such events as covalent interactions, ligand binding and other such reactions. This list is not meant to be inclusive. Other reactions, which are known in the art, will be evident to one of ordinary skill.

The compounds produced in the array may include, for example: a polymer, a catalyst, an organic compound, an amorphous material, a crystalline material, a smallmolecule, a pure material, a mixture of materials, bulk materials, particles of materials, thin films, a dispersion, an emulsion, a solution, an inorganic compound, a pharmaceutical, a sol-gel, a lubricant, a biological complex, covalent network solids, ionic solids, intermetallic materials, metal alloys, ceramic materials, organometallic materials, organic polymers, composite materials, and gases. The products may be of a biological nature, such as ligand-receptor, protein-protein, nucleic acid-nucleic acid, carbohydrate-protein, nucleic acid-protein complexes, various combinations of these, or others as are known in the art.

An embodiment of this invention relates to a combinatorial chemistry process where the temperature of the reaction can be modulated. For instance, the array may contain a plurality of thermal channels for providing a set of different temperatures to different rows within the array. Alternatively, the stage may further comprise thermocouples and means for maintaining isothermal conditions in at least one well, such as thermal channels.

In one embodiment of the invention, the combinatorial chemistry process may further comprise the steps of removing the array after the synthesizing step, wherein the array contains at least one compound in at least one well, placing the well array in an analytical instrument, and screening the compounds contained in the array. In this case, the analytical instrument is selected from any analytical instrument that is known in the art, including a reaction calorimeter, a differential scanning calorimeter, a viscosity sensor, a digital autoradiograph, or a mass spectrometer. As described in detail elsewhere, when the array is transferred between different stations, the array cover and the stage may need to be changed depending upon the technique to be used. Several of these instruments have been described in detail above.

Typical techniques to be used in this invention include, but are not limited to: chemical or biological testing, mass spectrometry, reaction calorimetry, parallel reaction calorimetry, parallel differential scanning calorimetry, viscosity measurement, thermogravimetric analysis (TGA), digital autoradiography, thermal imaging, polarimetry, imaging polarimetry, infrared spectroscopy, IR imaging, reflectance spectroscopy, uv-vis spectroscopy, chemisorption, surface area (BET) measurements, uv-vis fluorescence, phosphorescence, chemiluminescence, Raman spectroscopy, near IR spectroscopy, magnetic resonance imaging, NMR spectroscopy, Electron Spin Resonance (ESR) spectroscopy, gas chromatography, high performance liquid chromatography (HPLC), gel permeation chromatography (GPC), temperature rising elution fractionization (TREF), x-ray diffraction, neutron diffraction, refractometry, circular dichroism, turbidimetry, electron spectroscopy, scanning electron microscopy (SEM), transmitting electron microscopy (TEM), scanning tunneling microscopy (STM) and atomic force microscopy (AFM). These techniques may be used alone, or in any combination. The array can also be used for the measurement of chemical and physical properties such as magnetoresistance, conductivity, porosity, solubility, hexane extractables, weatherability, uv-vis stability, scratch resistance, abrasion resistance, wetability, hardness, color, dielectric constant, moisture absorption, drying rate, solvent swelling, gloss, adhesion, heat aging, shear, stain resistance, color fastness, scrub resistance, spreadability, emulsion stability, zeta potential, and contact angle. Any one of these techniques, taken alone or in combination with other techniques may be used in the practice of the invention.

In one embodiment of the invention, after the first reaction, the array may be optionally screened or characterized. If needed, any undesired side products may be removed, i.e. through evaporation, or other techniques known in the art. Then additional reagents may be added, and the next step of the synthesis may be carried out. In this manner, it may be possible to carry out a synthesis on the array, while screening and/or characterizing the intermediates as the synthesis progresses.

One embodiment of this invention relates to a polymerization process. In this instance, the array cover further comprises at least one gas manifold. In most instances, the reagents may be introduced via the gas manifold. Alternatively, the array cover provides a desired atmosphere. Typically, in this embodiment, a catalyst is first added to the wells of the array. The catalyst may be selected from a wide variety of catalysts, including heterogeneous catalysts, and homogeneous catalysts.

Typical catalysts include, but are not limited to: mixed metal oxides, mixed metal nitrides, mixed metal sulfides, mixed metal carbides, mixed metal fluorides, mixed metal silicates, mixed metal aluminates, mixed metal phosphates, Nobel metals, zeolites, metal alloys, intermetallic compounds, inorganic mixtures, inorganic compounds, inorganic salts, radical catalysts, cationic catalysts, anionic catalysts, organometallic catalysts and anionic coordination catalysts.

The catalysts may be dispensed by using a commercially available, robotic pipetter. Commercially available systems typically require 4.5 mm spacing between wells. Microfluidic apparatus may be desired for small well volumes. Initial experiments should involve control experiments to ensure that test results are not overly influenced by what position a particular catalyst occupied in the array. These control experiments depend largely on the specific apparatus and analyte but may include tests of blank wells, four identical quadrant arrays within one plate, and calibration of apparatus with known standards.

The monomers for polymerization may be selected from a wide variety of compounds, and include but are not limited to: ethylene, alpha-olefins such as propylene, 1-butene, 1-pentene, 1-hexene, and 1-octene, vinyl monomers such as vinyl chloride, vinyl acetate, vinyl acrylate, methylmethacrylate, methyl vinyl ether, ethyl vinyl ether, carbon monoxide, norbornene, bisphenol A, terephthalic acid, and acetonitrile. Typical oxidation substrates may include: methane, ethylene, ethane, propylene, propane, butene, butane, benzene, carbon monoxide.

IV. Screening and Characterization Methods

The invention relates to a number of methods for the screening and characterization of chemical compounds in libraries or arrays. A typical process involves the steps of providing an array, placing the array on a stage of a first analytical instrument and screening and/or characterizing the compounds in the array.

The array has been described in detail above. The array contains at least one compound in at least one well; for instance, there may be one compound in each well of the array, or each well may contain a mixture of compounds or reaction products. Individual compounds in the array, or the entire array as a whole, may be screened and characterized.

According to an embodiment of the invention, a first analytical instrument may be selected, in order to screen and/or characterize the compounds in the array. After this step, the compounds of interest may be identified in particular wells, and then the array be removed from the first analytical instrument and placed into a second analytical instrument for further characterization of compounds of interest. In this manner it is possible to collect a data on an entire array of compounds, in an efficient manner. As described elsewhere, when the array is moved between different stations, the array cover and/or stage may need to be removed and replaced as appropriate for each technique.

In another embodiment of the invention, after the first screening or characterizing step, the process further involves the steps of removing the array from the first analytical instrument, placing the array into a second analytical instrument, and screening and/or characterizing the compounds. The array may thus be interchanged between several different stations for a variety of characterization steps. In this manner, a large amount of data on each compound in the array may be generated.

In an embodiment of the invention, the compounds in the array are characterized in a highly parallel fashion, rather than sequentially. The methods described above are generally used in order to accomplish the characterization of more than one well at a time. However, the invention also relates to techniques which may be largely sequential, such as mass spectroscopy, where individual wells are analyzed well by well.

Typical analytical instruments include a camera, a reaction calorimeter, a parallel reaction calorimeter, a differential scanning calorimeter, a viscosity sensor, a stiffness sensor, a mass sensor, a thermogravimetric sensor, a digital radiography, and a mass spectrometer, and combinations of these. The term camera is used to broadly encompass a number of devices for detecting and recording electromagnetic signals. The camera comprises a suitable detector capable of responding to the desired radiation. For instance suitable detectors for infrared radiation include MCT or PtSi detectors. In some embodiments, the camera contains an array of detectors so that all samples are examined simultaneously. The camera may be selected from a variety of types of cameras. For example, the camera may be an infrared (IR) camera, ultraviolet (UV) camera, visible (Vis) camera, X-ray camera, electronic gradient camera, or any combination of these. The invention should not be limited to these instruments, and other possible instruments that are known in the art may also be used.

Typical screening and characterizing techniques to be used in this invention include, but are not limited to: chemical or biological testing, mass spectrometry, reaction calorimetry, parallel reaction calorimetry, parallel differential scanning calorimetry, viscosity measurement, thermogravimetric analysis (TGA), digital autoradiography, thermal imaging, polarimetry, imaging polarimetry, infrared spectroscopy, IR imaging, reflectance spectroscopy, uv-vis spectroscopy, chemisorption, surface area (BET) measurements, uv-vis fluorescence, phosphorescence, chemiluminescence, Raman spectroscopy, near IR spectroscopy, magnetic resonance imaging, NMR spectroscopy, Electron Spin Resonance (ESR) spectroscopy, gas chromatography, high performance liquid chromatography (HPLC), gel permeation chromatography (GPC), temperature rising elution fractionization (TREF), x-ray diffraction, neutron diffraction, refractometry, circular dichroism, turbidimetry, electron spectroscopy, scanning electron microscopy (SEM), transmitting electron microscopy (TEM), scanning tunneling microscopy (STM) and atomic force microscopy (AFM). These techniques may be used alone, or in any combination. The array can also be used for the measurement of chemical and physical properties such as magnetoresistance, conductivity, porosity, solubility, hexane extractables, weatherability, uv-vis stability, scratch resistance, abrasion resistance, wetability, hardness, color, dielectric constant, moisture absorption, drying rate, solvent swelling, gloss, adhesion, heat aging, shear, stain resistance, color fastness, scrub resistance, spreadability, emulsion stability, zeta potential, and contact angle. Any one of these techniques, taken alone or in combination with other techniques may be used in the practice of the invention.

In an embodiment of the invention, the array can be used for the rapid screening of olefin polymerization catalysts. Several techniques for the characterization of compounds in the array, which are not consumptive, and allow for multiple characterization steps on the same array are possible. Accordingly, the array allows for the rapid screening of various polymer catalysts, the rapid synthesis of combinatorial libraries of polymers, and the characterization of combinatorial polymer libraries. These methods will allow not only for the rapid discovery of new leads in polymer and catalyst chemistry, but also for rapid optimization of leads. The analysis of the combined data from several screenings and/or several characterizations of the library or array provides a quick means of correlating the effects of catalyst/cocatalyst structure and reaction conditions on many aspects of polymer properties. This data provides an understanding of catalyst behavior, which will in turn lead to more rational design of catalysts and, ultimately, better polymer performance at lower cost.

In addition, the invention is readily amenable to incorporation of more techniques for polymer analysis and the expansion of the arrays (and corresponding decrease in reactor well size) to much larger arrays (e.g., 10,000) for higher-throughput. The invention is also readily applicable to many classes of reactions and materials and different analysis applications.

V. Workstation

The invention relates to a workstation, which comprises various stages, and various synthetic and analytical instruments. According to the invention, the workstation comprises an array, which comprises a substrate having a plurality of wells, a series of stages to support the at least one array; and at least one unit, which is used in synthesis, screening, or characterization. According to the invention, the synthesis, screening and characterization steps may all be carried out in the workstation.

The units may be independently selected from the following units but not limited to, which have been described in detail above: a thermal imaging unit, a parallel reaction calorimeter unit, a parallel differential scanning calorimeter unit, a viscosity sensor unit, a stiffness sensor unit, a mass sensor unit, a thermogravimetric unit, an autoradiography unit, a mass spectrometry unit, and optionally, an inert atmosphere. Other units or instruments will may be included in the workstation will be apparent to one of ordinary skill in the art. In addition, the workstation may be connected to other instruments. For example, the workstation may be connected to a mass spectrometer.

An embodiment of the workstation is shown in FIG. 16. As shown, in one embodiment of the invention, the workstation will incorporate a thermal imaging unit (39), a camera (44), a parallel reaction calorimeter unit (40), a parallel differential scanning calorimetry unit (41), a viscosity/stiffness sensor (42), and an oven (51). Optionally, the workstation is housed in a drybox/glovebox (43), and may provide an inert atmosphere.

In an embodiment of the invention, the workstation will further comprising means for transferring the array from the first analytical instrument to a second analytical instrument. The array may thus be transferred and/or interchanged between a number of units. The process may also be automated or programmed. As shown in FIG. 16, there may be vial rack (45), plate rack positioned outside the workstation (46), micropipetter (47), handling tool (48), plate rack inside the workstation (49) and a tool rack (50) in this embodiment. Depending upon the nature of the combinatorial library, different units and different analysis will be desired, as will be evident to one of ordinary skill in the art.

In a preferred embodiment, the means for transferring the array is a robotic hand. The invention also includes an embodiment where the array is bar-coded, and/or where the workstation further comprising array hotels. In a preferred embodiment, the workstation is fully automated.

In an embodiment of the invention, the workstation is used in the development of new polymerization catalysts to provide better performing polymers at lower cost. In this embodiment, the workstation is constructed in a sealed glovebox. If necessary, an inert (i.e., nitrogen, argon, etc.) atmosphere may be used, if the polymerization catalysts or other reagents are sensitive to oxygen and/or moisture. Thermal imaging serves as a screen of catalyst activity. The activity of promising catalysts are then further analyzed in more detail, using instruments such as the parallel reaction calorimeter and mass spectrometer. The resulting polymers will then be characterized using the parallel differential scanning calorimeter, digital autoradiography, and/or the viscosity/stiffness sensor. Thus, the workstation is used to accelerate the development of new polymerization catalysts.

It should be understood that the foregoing discussion and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference The claimed invention is:

1. A parallel reaction calorimeter system comprising
   a. an the array, wherein the array comprises:
      i. a substrate having a plurality of wells wherein at least one well further comprises a membrane forming the bottom of the well; and
      ii. at least one thermal channel within the substrate to regulate the temperature in at least one of the wells wherein said thermal channel or thermal channels are proximate to, noncontiguous to, positioned between, and present in the same plane as at least two of said wells;
   b. a stage, comprising an array of sensors, wherein the array of sensors provide individual temperature control of each well; and
   c. at least one manifold disposed above at least one well.

2. A parallel reaction calorimeter system of claim 1, wherein the sensors are heat or temperature sensors.

3. A parallel reaction calorimeter system of claim 2, wherein the heat or temperature sensors provide for individual temperature control of each well.

4. A parallel reaction calorimeter system of claim 1, wherein the membrane is flexible, thermally conductive, or gas-permeable.

5. A parallel reaction calorimeter system of claim 1, wherein the array contains a plurality of thermal channels for maintaining different temperatures in different rows within the array.

6. A parallel reaction calorimeter system of claim 1, wherein the manifold is a gas manifold that provides different sets of gas feeds to different regions of the array.

7. A parallel reaction calorimeter system of claim 6, wherein the gas manifold provides different sets of gas pressures to different regions of the array.

8. A parallel reaction calorimeter system of claim 1, wherein the manifold comprises stainless steel.

9. A parallel reaction calorimeter system of claim 1, wherein the system further comprises at least one gold foil gasket around each well, wherein the gold foil gasket, together with the manifold, forms a seal around each well.

10. A process of characterizing compounds, comprising the steps of
    a. providing an array, wherein the array comprises:
       i. a substrate having a plurality of wells, wherein at least one well contains at least one compound, and
       ii. at least one thermal channel within the substrate to regulate the temperature in at least one of the wells, wherein said thermal channel or thermal channels are proximate to, noncontiguous to, positioned between, and present in the same plane as at least two of said wells; and
    b. placing the array on a parallel reaction calorimeter, wherein the parallel reaction calorimeter comprises:
       i. a stage comprising an array of sensors, wherein the array of sensors provide individual temperature control of each well; and
       ii. a manifold disposed above at least one well, and
    c. characterizing the at least one compound, wherein the characterizing step comprises the steps of:
       i. maintaining isothermal conditions in at least one well, and
       ii. monitoring the heat required to maintain isothermal conditions in the at least one well.

11. A differential scanning calorimeter system comprising
    a. an the array, wherein the array comprises:
       i. a substrate having a plurality of wells wherein at least one well further comprises a membrane forming the bottom of the well, and ii. at least one thermal channel within the substrate to regulate the temperature in at least one of the wells, wherein said thermal channel or thermal channels are proximate to, noncontiguous to, positioned between, and present in the same plane as at least two of said wells; and b. a stage comprising an array of sensors, wherein the array of sensors provide individual temperature control of each well, wherein the stage further comprises:
  i. at least one thermocouple attached to at least one well, and
  ii. at least one thermocouple for measuring the reference temperature of a reference compound,
  wherein the thermocouple measuring the reference temperature of the reference compound is attached in series to the at least one thermocouple attached to the at least one well.

12. A differential scanning calorimeter system of claim 11, wherein the sensors are heat or temperature sensors.

13. A differential scanning calorimeter system of claim 12, wherein the heat or temperature sensors provide for individual temperature control of each well.

14. A differential scanning calorimeter system of claim 11, wherein the membrane is flexible, thermally conductive, or gas-permeable.

15. A differential scanning calorimeter system of claim 11, wherein the array contains a plurality of thermal channels for providing a set of different temperatures to different rows within the array.

16. A process of characterizing compounds, comprising the steps of
a. providing an array, wherein the array comprises a substrate having a plurality of wells, wherein at least one compound is present in at least one well, and wherein at least one well further comprises a membrane forming the bottom of the well;
b. placing the array on a differential scanning calorimeter system, wherein the differential scanning calorimeter system comprises:
  i. a stage, comprising an array of sensors, wherein the array of sensors provide individual temperature control of each well;
  wherein the stage is a heating stage further comprising at least one thermocouple attached to at least one well and at least one thermocouple measuring the reference temperature of a reference compound,
  wherein the thermocouple measuring the reference temperature of the reference compound is attached in series to the at least one thermocouple attached to the at least one wells; and
  ii. a manifold disposed above at least one well; and
c. characterizing the at least one compound, wherein the characterizing step comprises the steps of:
  i. maintaining isothermal conditions in at least one well;
  ii. monitoring the heat required to maintain isothermal conditions in the at least one well;
  iii. optionally, removing any materials other than the compound to be characterized;
  iv. heating the compound and the reference compound at a constant rate;
  v. maintaining the temperature of the compound equal to the temperature of the reference compound; and
  vi. measuring the differences in heat fluxes required to keep the temperature of the compound equal to the temperature of the reference compound.

* * * * *